(12) United States Patent
Trumbore et al.

(10) Patent No.: US 9,018,236 B2
(45) Date of Patent: Apr. 28, 2015

(54) CYCLODEXTRIN-BASED MICROEMULSIONS, AND DERMATOLOGICAL USES THEREOF

(71) Applicant: Precision Dermatology, Inc., Cumberland, RI (US)

(72) Inventors: Mark W. Trumbore, Westford, MA (US); Pinaki Ranjan Majhi, Sharon, MA (US); Dinen Divyang Shah, Woonsocket, RI (US)

(73) Assignee: Precision Dermatology, Inc., Cumberland, RI (US)

( * ) Notice: Subject to any disclaimer, the term of this patent is extended or adjusted under 35 U.S.C. 154(b) by 0 days.

(21) Appl. No.: 13/803,280

(22) Filed: Mar. 14, 2013

(65) Prior Publication Data

US 2013/0253014 A1  Sep. 26, 2013

Related U.S. Application Data

(60) Provisional application No. 61/614,177, filed on Mar. 22, 2012.

(51) Int. Cl.

| | |
|---|---|
| *A61K 47/40* | (2006.01) |
| *A61K 31/455* | (2006.01) |
| *A61K 8/73* | (2006.01) |
| *A61Q 19/08* | (2006.01) |
| *A61K 31/07* | (2006.01) |
| *A61K 8/67* | (2006.01) |
| *A61K 8/39* | (2006.01) |
| *A61K 8/06* | (2006.01) |
| *A61K 9/00* | (2006.01) |
| *A61K 9/107* | (2006.01) |

(52) U.S. Cl.
CPC ............... *A61K 47/40* (2013.01); *A61K 8/738* (2013.01); *A61Q 19/08* (2013.01); *A61K 31/07* (2013.01); *A61K 8/671* (2013.01); *A61K 31/455* (2013.01); *A61K 8/39* (2013.01); *A61K 8/068* (2013.01); *A61K 9/0014* (2013.01); *A61K 9/1075* (2013.01)

(58) Field of Classification Search
CPC ....... A61K 8/39; A61K 8/068; A61K 9/0014; A61K 9/1075; A61K 31/455; A61K 8/671; A61K 31/07; A61K 8/738

See application file for complete search history.

(56) References Cited

U.S. PATENT DOCUMENTS

| | | | |
|---|---|---|---|
| 7,781,489 B2 * | 8/2010 | Menegatti et al. ............ | 514/725 |
| 2002/0176877 A1 | 11/2002 | Cole et al. | |
| 2005/0266085 A1 * | 12/2005 | Warner et al. ................. | 424/486 |
| 2008/0206155 A1 | 8/2008 | Tamarkin et al. | |
| 2009/0131375 A1 | 5/2009 | Gross | |
| 2009/0232743 A1 * | 9/2009 | Varanasi et al. ............... | 424/45 |
| 2012/0003163 A1 | 1/2012 | Mordas et al. | |

OTHER PUBLICATIONS

Nandi et al. in AAPS PharmSciTech: 4(1), 1-9 (2003).*
Dalmora et al. in International Journal of Pharmaceutics 184 (1999) 157-164.*
Draelos et al. in Journal of Cosmetic and Laser Therapy, 8:96-101 (2006).*
Fahr et al., "Drug delivery strategies for poorly water-soluble drugs," Expert Opinion on Drug Delivery, 14(4):403-416 (2007).
Furlanetto et al., "Mixture experiment methods in the development and optimization of microemulsion formulations," Journal of Pharmaceutical and Biomedical Analysis, 55:610-617 (2011).
Wu et al., "Tissue compatibility and pharmacokinetics of three potential subcutaneous injectables for low-pH drug solutions," Journal of Pharmacy and Pharmacology, 62:873-882 (2010).
International Search Report dated Jun. 28, 2013, from PCT/US2013/031296.
International Search Report dated Jun. 28, 2013, from PCT/US2012/031292.
International Search Report dated Jun. 26, 2013, from PCT/US2012/031303.
Nandi et al.: "Synergistic Effect of PEG-400 and Cyclodextrin to Enhance Solubility of Progesterone," AAPS PharmSciTech 2003; 4(1) Article 1 (http://www.pharmscitech.org) (5 pages).

* cited by examiner

*Primary Examiner* — Dennis Heyer
(74) *Attorney, Agent, or Firm* — Brian B. Shaw; John E. Thomas; Toan P. Vo

(57) ABSTRACT

Described herein are cyclodextrin-stabilized microemulsion systems useful for increasing the solubility, stability, bioavailability, or safety of an active agent for delivery to the skin. The microemulsions may reduce the occurrence of skin irritation or odor upon application.

19 Claims, 16 Drawing Sheets

Figure 3
(a)
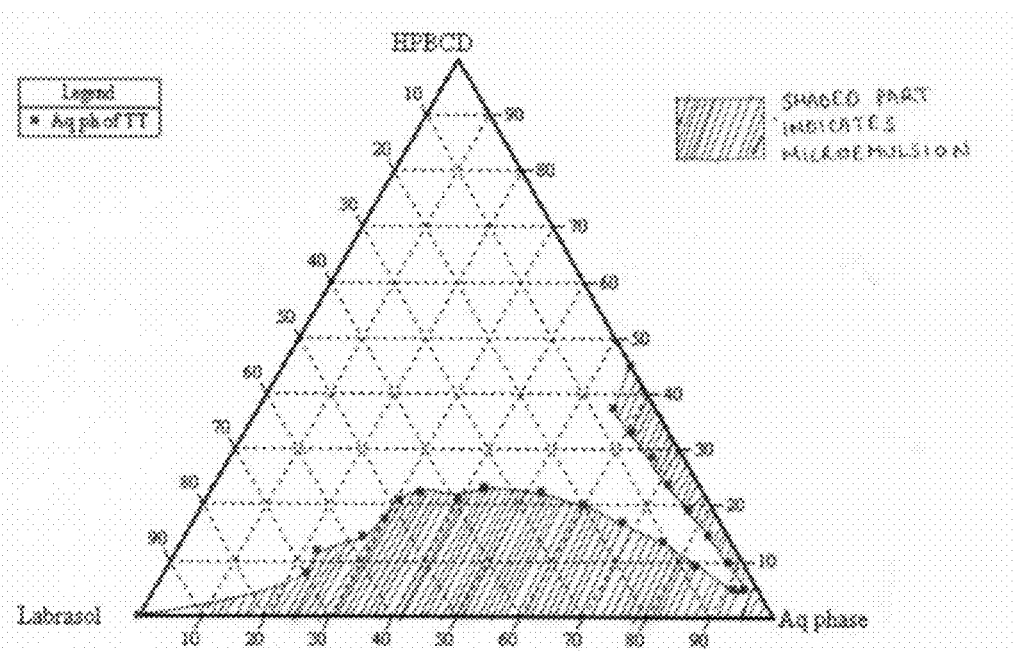
(b)
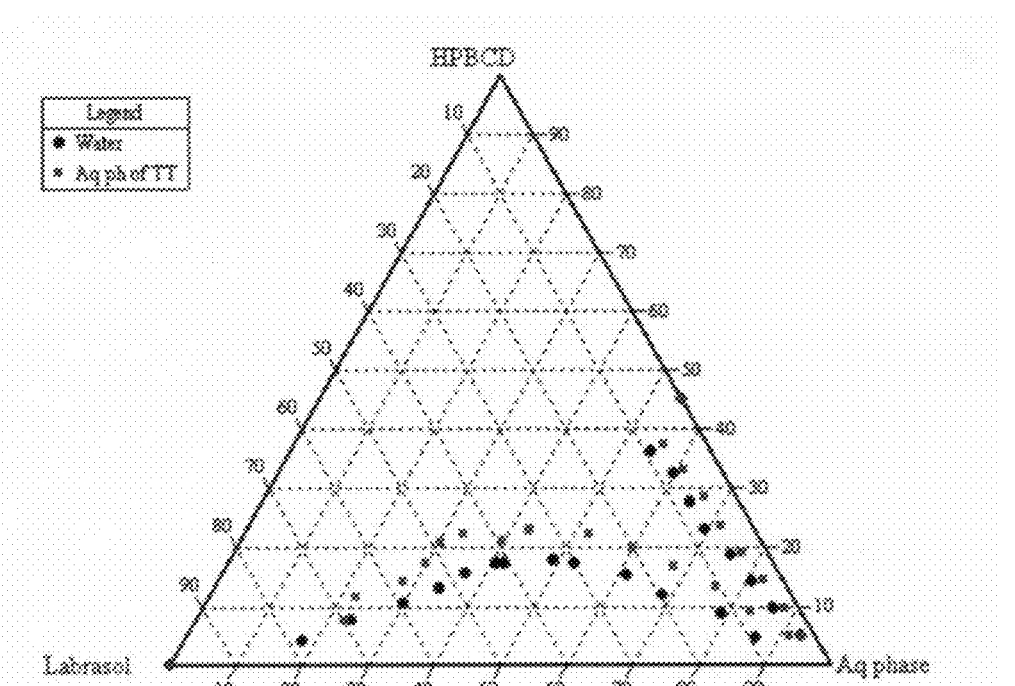

Figure 4
(a) 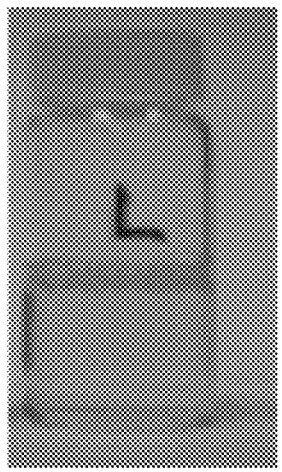
(b) 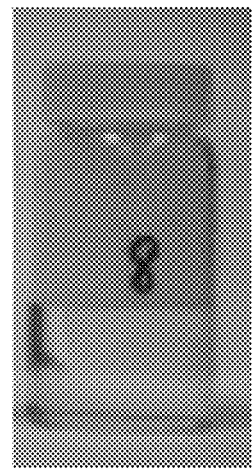
(c) 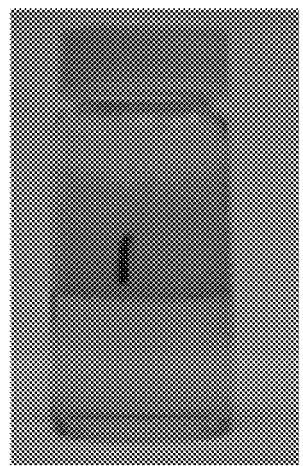

| Ingredients | % w/w |
|---|---|
| DI Water | 91.62 |
| Pentylene Glycol (Hydrolite-5) | 4.5 |
| Allantoin | 0.4 |
| 1% sodium hyaluronate sol'n | 1 |
| Panthenol DL | 1 |
| Niacinamide | 1 |
| Potassium Sorbate | 0.15 |
| Sodium Benzoate | 0.15 |
| Disodium EDTA | 0.1 |
| Sodium Hydroxide 50% S | 0.08 |
| Total | 100 |

| Ingredients | %w/w |
|---|---|
| Water | 80 |
| Labrasol® | 15 |
| Hydroxy Propyl Beta Cyclodextrin | 5 |

(b)

| Ingredients | %w/w |
|---|---|
| Water | 90 |
| Labrasol® | 7 |
| Hydroxy Propyl Beta Cyclodextrin | 3 |

Figure 7

| 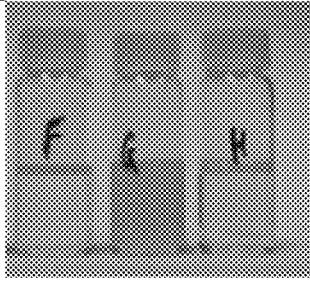 | 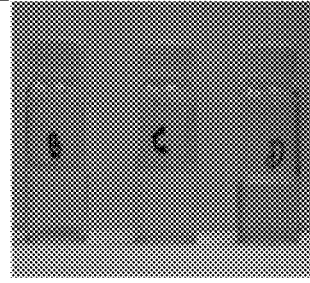 | 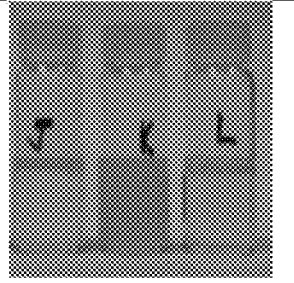 |
|---|---|---|
| HP-alfa-CD | HP-beta-CD | HP-gamma-CD |

| In each panel - |
|---|
| Left: 1.2% Retistar in water |
| Middle: 1.2% Retistar in water with 5% hydroxypropyl-x-cyclodextrin |
| Right: 1.2% Retistar in water with 15% Labrasol® and 5% hydroxypropyl-x-cyclodextrin |
| Final retinol concentration: 0.06% |

| 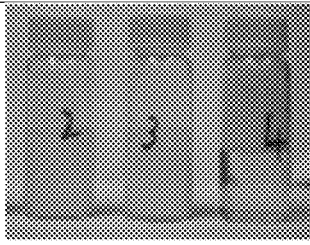 | 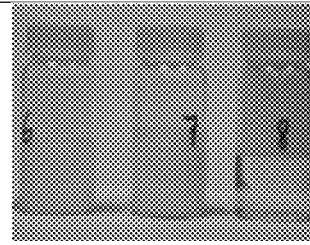 | 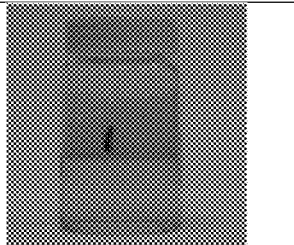 |
|---|---|---|
| HP-alfa-CD | HP-gamma-CD | HP-gamma-CD |

| In each panel - | 1.2% solid retinol dissolved in water with 15% Labrasol® and 5% hydroxypropyl-gamma-cyclodextrin |
|---|---|
| Left: 2.66% Retinol 50C in water | |
| Middle: 2.66% Retinol 50C in water with 5% hydroxypropyl-x-cyclodextrin | |
| Right: 2.66% Retinol 50C in water with 15% Labrasol® and 5% hydroxypropyl-x-cyclodextrin | |
| Final retinol concentration: 1.2% | |

Figure 10

| Ingredients | % w/w |
|---|---|
| Phase A: | |
| BHT | 0.10 |
| Stearyl glycyrrhetinate (NET-STG) | 0.10 |
| Dipalmitoyl hydroxyproline (Sepilift DPHP) | 1.00 |
| Cetyl alcohol + glyceryl stearate + PEG-75 stearate + ceteth-20 + steareth-20 (Emulium Delta) | 5.00 |
| Cetyl Alcohol NF | 1.00 |
| Jojoba wax + sunflower wax = mimosa wax (Hydracire S) | 2.00 |
| Isononyl Isononanoate | 6.00 |
| Shea Butter | 2.00 |
| C12-C15 alkyl ethylhexanoates (Activemol EH-25) | 4.00 |
| Vitamin E Acetate (tocopheryl acetate) | 0.50 |
| Tetrahexyldecyl ascorbate (BV-OSC) | 0.50 |
| Dragosantol 100 | 0.20 |
| Silicone, 200/350→ used only dimethicone medical fluid RM 8070 | 1.50 |
| Dimethicone + divinyldimethicone + silsesquioxane cross polymer (Gransil SLIP 1) | 1.50 |
| Caprylic/Capric Triglyceride | 2.00 |
| | |
| Phase B: | |
| Microemulsion system (containing Retinol) | 55.19 |
| Magnesium aluminum silicate (Veegum K Granules) (Thickener) | 0.60 |
| | |
| Phase C: | |
| Pentylene glycol (Hydrolite 5) | 4.50 |
| Xanthan Gum # 80 (Thickener) | 0.10 |
| (continued on next page) | |

Figure 10, continued

| Ingredients | % w/w |
|---|---|
| Phase D: | |
| Allantoin | 0.40 |
| Sodium hyaluronate, 1% (Macronan S PF) | 1.00 |
| Panthenol DL | 1.00 |
| Niacinamide | 1.00 |
| Potassium Sorbate | 0.15 |
| Sodium Benzoate | 0.15 |
| Disodium EDTA (Versene NA 2) | 0.10 |
| Sodium Hydroxide 50% S | 0.08 |
| | |
| Phase E: | |
| Glycerin + palmitoyl dipeptide-5 diaminobutyloyl hydroxythreonine + palmitoyl dipeptide-6 diaminohydroxybutyrate (Syn-Tacks) | 1.00 |
| Palmitoyl-lysyl-valyl-lysine bistrifluoroacetate + glycerin (Syn-Coll) | 2.50 |
| Butylene glycol + hydrolyzed rice extract (Aquarize IS) | 1.00 |
| Algae extract + mugwort extract (Triple A Complex) | 1.00 |
| | |
| Phase F: | |
| Pentylene glycol (Hydrolite 5) | .50 |
| (3-(4-chlorophenoxy)-2-hydroxypropyl)carbamate (Chlorphenesin Powder) | .30 |
| | |
| Phase G: | |
| Sodium Ascorbate | 0.24 |
| DL Tocopherol | 0.16 |
| | |
| Phase H: | |
| Retinol 50C (Added as Phase B) | 1.33 |
| | |
| Phase I: | |
| Bergamot M1500 | 0.3 |
| | |
| Total | 100 |

For all 3 pictures, to the Left is the Microemulsion batch (1083-15)

To the right is the control batch (1083-17)

Figure 13

| Ingredients | Retinol Transforming treatment (0.5%) NB 1083-15 | Retinol Transforming treatment (0.5%) 1083-27 | Retinol Transforming treatment (0.075%) 1083-30 | Retinol Transforming treatment (0.5%) 1083-33 | Retinol Transforming treatment (0.075%) 1083-36 |
|---|---|---|---|---|---|
| | | | %w/w | | |
| Microemulsion system B | - | - | 55.94 | - | 58.84 |
| Microemulsion system A | 55.19 | 54.92 | - | 57.82 | - |
| Isononyl Isononanoate | 6.00 | 6.00 | 6.00 | 4.00 | 4.00 |
| cetyl alcohol + glyceryl stearate + PEG-75 stearate + ceteth-20 + steareth-20 | 5.00 | 5.00 | 5.00 | 5.00 | 5.00 |
| Pentylene glycol – 5% | 5 | 5 | 5 | 5 | 5 |
| C12-C15 alkyl ethylhexanoates | 4.00 | 4.00 | 4.00 | 2.00 | 2.00 |
| Palmitoyl-lysyl-valyl-lysine bistrifluoroacetate + glycerin | 2.50 | 2.50 | 2.50 | 2.50 | 2.50 |
| Jojoba wax + sunflower wax + mimosa wax | 2.00 | 2.00 | 2.00 | 2.00 | 2.00 |
| Shea Butter | 2.00 | 2.00 | 2.00 | 2.00 | 2.00 |
| Caprylic/Capric Triglyceride | 2.00 | 2.00 | 2.00 | 2.00 | 2.00 |
| Polydimethylsiloxane (Silicone), 200/350 | 1.50 | 1.50 | 1.50 | 1.50 | 1.50 |
| Dimethicone + divinyldimethicone + silsesquioxane cross polymer | 1.50 | 1.50 | 1.50 | 1.50 | 1.50 |
| Dipalmitoyl hydroxyproline | 1.00 | 1.00 | 1.00 | 1.00 | 1.00 |
| Cetyl Alcohol NF | 1.00 | 1.00 | 1.00 | 1.50 | 1.50 |
| Sodium hyaluronate, 1% | 1.00 | 1.00 | 1.00 | 1.00 | 1.00 |
| Panthenol DL | 1.00 | 1.00 | 1.00 | 1.00 | 1.00 |
| Niacinamide | 1.00 | 1.00 | 1.00 | 1.00 | 1.00 |
| Butylene glycol + hydrolyzed rice extract | 1.00 | 1.00 | 1.00 | 1.00 | 1.00 |
| (continued on next page) | | | | | |

Figure 13, continued

| | | | | | |
|---|---|---|---|---|---|
| Algae extract + mugwort extract | 1.00 | 1.00 | 1.00 | 1.00 | 1.00 |
| Glycerin + palmitoyl dipeptide-5 diaminobutyloyl hydroxythreaonine + palmitoyl dipeptide-6 diaminohydroxybutyrate | 1.00 | 1.00 | 1.00 | 1.00 | 1.00 |
| Magnesium aluminum silicate Granules | 0.60 | 1.00 | 1.00 | 1.50 | 1.50 |
| Vitamin E Acetate (tocopheryl acetate) | 0.50 | 0.50 | 0.50 | 0.50 | 0.50 |
| Tetrahexyldecyl Ascorbate | 0.50 | 0.50 | 0.50 | 0.50 | 0.50 |
| Allantoin | 0.40 | 0.40 | 0.40 | 0.40 | 0.40 |
| Bergamot M1500 | 0.30 | 0.30 | 0.30 | 0.30 | 0.30 |
| (3-(4-chlorophenoxy)-2-hydroxypropyl)carbamate | 0.30 | 0.30 | 0.30 | 0.30 | 0.30 |
| Sodium Ascorbate | 0.24 | 0.24 | 0.24 | 0.24 | 0.24 |
| bisabolol | 0.20 | 0.20 | 0.20 | 0.20 | 0.20 |
| DL Tocopherol | 0.16 | 0.16 | 0.16 | 0.16 | 0.16 |
| Potassium Sorbate | 0.15 | 0.15 | 0.15 | 0.15 | 0.15 |
| Sodium Benzoate | 0.15 | 0.15 | 0.15 | 0.15 | 0.15 |
| BHT | 0.10 | 0.10 | 0.10 | 0.10 | 0.10 |
| Stearyl Glycyrrhetinate | 0.10 | 0.10 | 0.10 | 0.10 | 0.10 |
| Xanthan Gum # 80 | 0.10 | 0.10 | 0.10 | 0.20 | 0.20 |
| Disodium EDTA | 0.10 | 0.10 | 0.10 | 0.10 | 0.10 |
| Sodium Hydroxide 50% S | 0.08 | 0.08 | 0.08 | 0.08 | 0.08 |
| Retinol 50C (Added as Microemulsion) | 1.33 | 1.20 | 0.18 | 1.20 | 0.18 |
| Total | 100.00 | 100.00 | 100.00 | 100.00 | 100.00 |

Figure 14

| Ingredients | Retinol Cream (0.5%) NB 1083-25 | Retinol Cream (0.5%) NB 1083-39 |
|---|---|---|
| Microemulsion System A | 92.71 | 64.14 |
| Diethyl Sebacate | - | 8.00 |
| Glycerin | - | 7 |
| Isostearyl Alcohol | - | 4.00 |
| Cetostearyl Alcohol | 0.50 | 3.00 |
| Emulsifying wax | 2.30 | 3.00 |
| Brij 76 (Polyoxyethylene (10) Stearyl Ether) | 0.69 | 2.00 |
| Pentylene Glycol | - | 2.5 |
| Dimethicone | 2.00 | 2.00 |
| Niacinamide | - | 1 |
| Sodium Phosphate | - | 1 |
| Methyl Paraben | - | 0.3 |
| Propyl Paraben | - | 0.1 |
| Sodium Hydroxide | - | 0.03 |
| Disodium EDTA | - | 0.1 |
| BHT | - | 0.03 |
| Retinol 50C (Added as Microemulsion) | 1.2 | 1.2 |
| Total | 100.00 | 100.00 |

Figure 15

| Ingredients | Retinol Gel (0.5%) |
| --- | --- |
|  | NB 1083-23 |
| Microemulsion System (Water: Labrasol®: HPGCD:: 80:15:05) | 98.2 |
| Carbopol Ultrez 20 (Acrylates/C10-30 Alkyl Acrylate Crosspolymer) | 1 |
| Phenoxyethanol | 0.8 |
| Retinol 50C (Added as Microemulsion) | 1.2 |
| Total | 100 |

Figure 16

| Conditions | % Label Claim of Retinol | |
| --- | --- | --- |
|  | Microemulsion cream (0.5% retinol) | Control cream (0.5% retinol) |
| Lot # | NB 1083-15 | NB 1083-17 |
| T=0 | 100.00 | 100.00 |
| 2 weeks at 40 °C | 92.83 | 91.96 |
| 1 month at 40 °C | 86.15 | 82.39 |
| 2 months at 40 °C | 82.02 | 72.74 |

CYCLODEXTRIN-BASED MICROEMULSIONS, AND DERMATOLOGICAL USES THEREOF

RELATED APPLICATIONS

This application claims the benefit of priority to U.S. Provisional Patent Application Ser. No. 61/614,177, filed Mar. 22, 2012, the contents of which are hereby incorporated by reference.

BACKGROUND

Microemulsions are thermodynamically-stable, optically-clear emulsions having submicron-sized droplets suspended in a continuous phase. These emulsions form spontaneously, and typically consist of an aqueous phase, an organic phase, and a surfactant/co-surfactant component.

Previous data suggest that volatile lower alcohols, such as ethanol, are required to maintain stable oil-in-water microemulsions. However, topical application of volatile lower alcohols has a drying effect on the skin. Additionally, volatile lower alcohols and compositions containing them are extremely flammable. For these reasons, volatile lower alcohol-containing microemulsions for topical application have seen limited commercial use.

Developing a formulation for a water-immiscible drug that displays desirable drug delivery and solubilization characteristics while meeting other formulation criteria, such as targeted drug concentration, drug stability, bioavailability, safety, and others, is challenging. Currently, many drug delivery systems are available, including liposomes, polymeric/surfactant aggregates, microemulsions. However, these systems have numerous shortcomings, such as low efficiency (e.g., low bioavailability of drug), heterogeneity, and instability of the delivery systems themselves.

There exists a need for a drug delivery vehicle for topical administration wherein a water-immiscible drug may be encapsulated or solubilized.

SUMMARY OF THE INVENTION

In certain embodiments, the invention relates to a microemulsion, consisting essentially of: an aqueous phase; a first surfactant; and a second surfactant, wherein the first surfactant is a cyclodextrin or a derivative of a cyclodextrin.

BRIEF DESCRIPTION OF THE FIGURES

FIG. 3 depicts ternary phase diagrams of systems containing (1) aqueous phase (squares; see FIG. 5 for compositions); and (2) pure water (black circles). The shaded portions of (a) indicate the existence of a microemulsion.

FIG. 4(a) depicts a Labrasol®-HPGCD-water microemulsion system, which is transparent, containing retinol (from Retistar) in a final concentration of 0.06%. This micro emulsion also contains capric/caprylic triglycerides.

FIG. 4(b) depicts a Labrasol®-HPGCD-water microemulsion system, which is transparent, containing retinol (from Retinol 50C) in a final concentration of 1.2%. This microemulsion also contains capric/caprylic triglycerides. The miscibility of retinol in this composition may be attributed to either or both of the cyclodextrin system and the micro emulsion system.

FIG. 4(c) depicts a Labrasol®-HPGCD-water microemulsion system, which is transparent, containing solid retinol in a final concentration of 1.2%. The miscibility of retinol in this composition may be attributed to either or both of the cyclodextrin system and the micro emulsion system.

FIG. 5 tabulates the composition of a representative aqueous phase.

FIG. 6 tabulates the compositions of (a) a microemulsion of the invention (microemulsion A); and (b) a second microemulsion of the invention (microemulsion B).

FIG. 7 depicts (top row, left to right, final retinol concentration=0.06%) 1.2% Retistar in water (F); 1.2% Retistar in water with 5% HPACD (G); 1.2% Retistar in water with 15% Labrasol® and 5% HPACD (H); 1.2% Retistar in water (B); 1.2% Retistar in water with 5% HPBCD (C); 1.2% Retistar in water with 15% Labrasol® and 5% HPBCD (D); 1.2% Retistar in water (J); 1.2% Retistar in water with 5% HPGCD (K); 1.2% Retistar in water with 15% Labrasol® and 5% HPGCD (L); and (bottom row, left to right, final retinol concentration=1.2%) 2.66% Retinol 50C in water (2); 2.66% Retinol 50C in water with 5% HPACD (3); 2.66% Retinol 50C in water with 15% Labrasol® and 5% HPACD (4); 2.66% Retinol 50C in water (6); 2.66% Retinol 50C in water with 5% HPGCD (7); 2.66% Retinol 50C in water with 15% Labrasol® and 5% HPGCD (8); and 1.2% solid retinol in water with 15% Labrasol® and 5% HPGCD (1).

FIG. 10 tabulates the components and weight percentage of each component in an exemplary cream formulation.

FIG. 13 tabulates the components and the weight percentage of each component in an exemplary cream formulation, which uses a retinol-transforming treatment vehicle.

FIG. 14 tabulates the components and the weight percentage of each component in an exemplary cream formulation, which comprises retinol as the active agent.

FIG. 15 tabulates the components and the weight percentage of each component of a microemulsion-based gel formulation (using retinol as the active agent).

FIG. 16 tabulates the results from chemical stability testing for 2 weeks at 40° C. for compositions with and without the benefit of an inventive microemulsion.

DETAILED DESCRIPTION OF THE INVENTION

Overview

Figure 1:
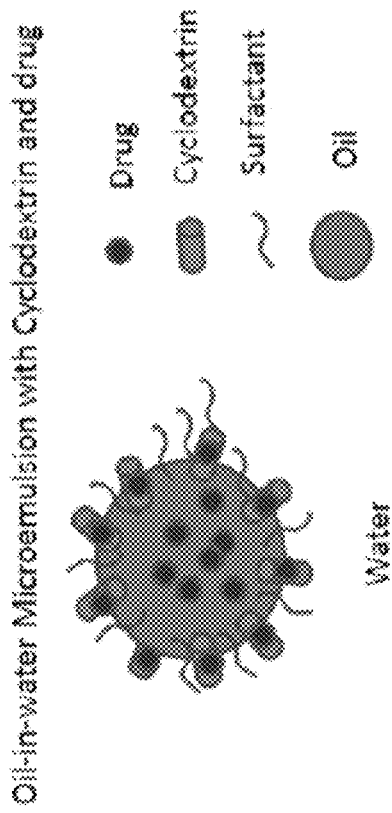
FIG. 1 depicts a schematic of an example of an oil-in-water microemulsion with cyclodextrin and drug molecules.
Figure 2:
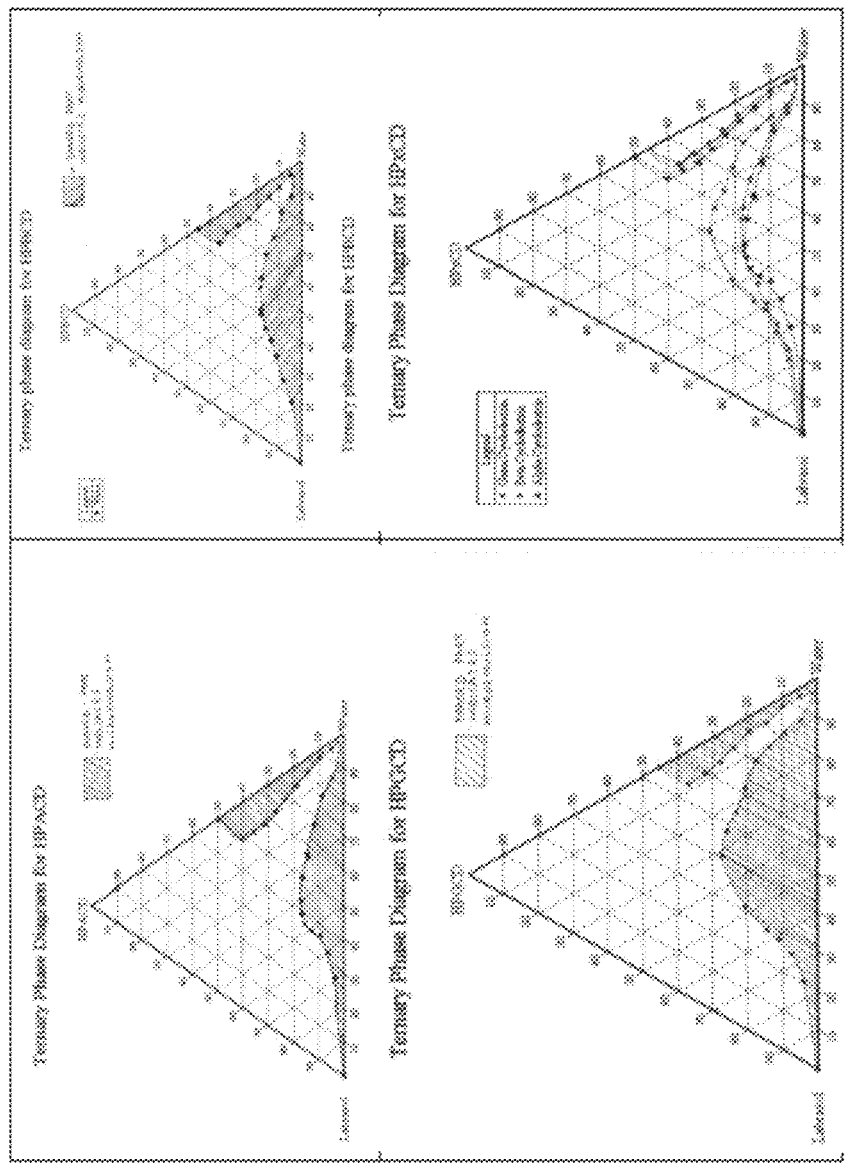
FIG. 2 depicts ternary phase diagrams developed from systems with Labrasol® (caprylocaproyl macrogol-8 glycerides and/or caprylocaproyl polyoxyl-8 glycerides), hydroxypropyl X-cyclodextrin (where X=alpha, beta, or gamma; HPxCD), and pure water. The shaded portions indicate the existence of micro emulsions.

In certain embodiments, the invention relates to the use of cyclodextrins (CDs) as a co-surfactant in microemulsion formulations free of volatile lower alcohols.

In certain embodiments, the invention relates to cyclodextrin-stabilized microemulsion formulations. In certain embodiments, the cyclodextrin-stabilized microemulsion formulations display desirable properties, such as increased drug solubility, stability, bioavailability, safety, reduced skin irritation, and the ability to mask odors.

In certain embodiments, the invention relates to any one of the aforementioned microemulsions, wherein the microemulsion does not comprise methanol, ethanol, propanol, or butanol.

In certain embodiments, the active agent-containing microemulsion formulation, upon mixing with a propellant in a pressurized container, remains a single-phase, optically-clear microemulsion. In certain embodiments, upon actuation from an aerosol container, microemulsion formulations of the present invention produce foam.

CD-Stabilized Microemulsions

In certain embodiments, the invention relates to a surfactant combination in aqueous solution that displays phase behavior characteristic of microemulsions, i.e., spontaneous formation of optically clear solutions when mixed in the proper ratios. While it has been reported that cyclodextrins are able to stabilize conventional oil-in-water emulsions, there have been no reports of cyclodextrins serving as co-surfactants stabilizing microemulsions. In certain embodiments, conventional oil-in-water emulsions and microemulsions are similar in that they both consist of oil droplets dispersed in an aqueous phase; however, they exhibit specific and fundamental differences. First, the oil droplet size in a microemulsion is one or more orders of magnitude smaller than the smallest droplet size achievable in a conventional emulsion. Second, conventional emulsions are thermodynamically unstable and require significant energy input to be created; in contrast microemulsions are thermodynamically stable and can form spontaneously with minimal mixing.

In certain embodiments, studies of the phase behavior of a caprylocaproyl polyethylene glycol surfactant/cyclodextrin/water system demonstrated the characteristic phase behavior properties of a microemulsion (FIGS. 1-4). In certain embodiments, the microemulsions of the invention also satisfy the physical characteristics of a typical microemulsion systems, such as: spontaneous formation, a clear isotopic solution, stability, or others. In certain embodiments, areas under the curve (FIG. 2, lined) represent the clear/single phase microemulsion systems. In certain embodiments, compositions outside the phase boundary lines are opaque/heterogeneous emulsion systems. In certain embodiments, much like established microemulsion systems, the inventive microemulsion systems required minimal shaking (simple vortexing or manual shaking) for formation and remained stable when thermodynamically controlled. From the phase diagram, it is hypothesized that the total area covering the clear phase, i.e., the microemulsion zone, increases as the core diameter of the cyclodextrin increases (i.e., HPACD<HPBCD<HPGCD). In certain embodiments, caprylocaproyl macrogol-8 glycerides and/or caprylocaproyl polyoxyl-8 glycerides (Labrasol®), an oily liquid with amphiphilic properties and dispersible in water, is treated as an oil in this Labrasol®-HPXCD-water systems. In certain embodiments, appropriate quantities of other oily/amphiphilic solvent(s)/surfactant(s) (e.g., caprylic/capric triglyceride, Spans, Tween, isopropyl myristate, oleic acid, diethyl sebacate, transcutol, etc.) can be added to these systems while maintaining the integrity of the microemulsion. In certain embodiments, additional co-solvents (e.g., propylene glycol, ethanol, hexylene glycol) or the ingredients (e.g., urea, salt, sorbitol) may be added to see the effect of the microemulsion phase boundary lines and hence the drug solubility (when applicable) in the reported systems.

Encapsulation of Active Agents in CD-Stabilized Microemulsions

In certain embodiments, a microemulsion as described herein may be useful in delivering water-immiscible ingredients. In certain embodiments, a model drug is retinol. Retinol is immiscible in water and commercially available as a dispersion in oil or surfactant medium (e.g., Retistar® and Retinol 50 C, respectively). Solid Retinol is also commercially available, but requires very low temperature storage conditions to avoid physical and chemical instability. In certain embodiments, using the cyclodextrin-based microemulsions of the invention, it is possible to incorporate into the systems greater than 1.0 wt % of retinol. In certain embodiments, the cyclodextrin-based microemulsion systems allow retinol to be sheltered inside the core of the cyclodextrin, as well as inside the microemulsion core. In certain embodiments, and not wishing to be bound by any particular theory, the dual-shelter structure may increase the thermodynamic activity of the drug molecules, and thus enhance drug release from vehicles (bioavailability). In certain embodiments, the encapsulation of a drug using the above method can be used to address a drug's solubility or stability, to enhance bioavailability, to reduce skin irritation, to increase safety, or to mask odors. In certain embodiments, other water-immiscible drugs or cosmetic ingredients can benefit from this system. In certain embodiments, molecules that may benefit from this system include, but are not limited to, Retinol, Colchicine, Benzoyl peroxide, Hydroquinone, Tretinoin, Clobetasol propionate, and Adapalene.

In certain embodiments, the drug encapsulation method is useful for the delivery of other water-immiscible drugs using topical (for example, dermal or transdermal), parental, ocular, nasal, rectal, or other routes of drug delivery. In certain embodiments, the systems can be used for controlled drug delivery using the advantage of simultaneous drug encapsulation in two different systems (i.e., microemulsion and cyclodextrin).

Semi-Solid and Foam Formulations Containing CD-Stabilized Microemulsions of Active Agents In certain embodiments, the invention relates to a method of formulating a semi-solid cyclodextrin-based microemulsion system, wherein the cyclodextrin-based microemulsion comprises an encapsulated water-immiscible drug. In certain embodiments, the invention relates to a method of increasing drug loading in a semi-solid or foam formulation by using the cyclodextrin-based microemulsion system.

In certain embodiments, the invention relates to a cream or lotion formulation comprising a cyclodextrin-based microemulsion system. In certain embodiments, the invention relates to a method of making the cream or lotion formulation. In certain embodiments, the cream or lotion formulation is useful for topical and other applications. In certain embodiments, the cyclodextrin-based microemulsion system comprises the aqueous phase of the cream/lotion. In certain embodiments, the oil phase of the cream/lotion, is immiscible with the microemulsion system. In certain embodiments, the cream may be thickened using oil or a water-miscible thickener that does not destabilize the microemulsion. In certain embodiments, additional loading of the drug is possible when the thickener is selected from the group consisting of chitosan, sodium alginate, and block copolymers that also have ability to solubilize the drug.

In certain embodiments, the invention relates to an aerosol foam formulation comprising a cyclodextrin-based microemulsion system. In certain embodiments, the aerosol foam formulation comprises the aforementioned cream formulation and a propellant.

In certain embodiments, the invention relates to a non-aerosol foam formulation comprising a cyclodextrin-based microemulsion system. In certain embodiments, additional surfactant or foam boasting ingredient may be added (to achieve the desired foam quality) as long as the microemulsion remains intact.

DEFINITIONS

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Exemplary Constituents of Emulsions and Compositions of the Invention

Exemplary identities of various constituents of the compositions of the present invention are described below.

1. Propellants

In certain embodiments, the propellant is a HFA or a mixture of one or more hydrofluorocarbons. Suitable hydrofluorocarbons include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. The concentration of the HFA propellant is from about 2% to about 50% by weight of the composition. In certain embodiments, the propellant comprises a hydrofluoroolefin (HFO), or a mixture of HFO and HFA. Suitable hydrofluoroolefins include 1,3,3,3-tetrafluoropropene (HFO 1234ze) and mixtures and admixtures of this and other HFO suitable for topical use. The concentration of the HFO propellant is from about 2% to about 50% by weight of the composition. Hydrocarbon as well as CFC propellants can also be used in the present invention.

2. Vehicles

Suitable topical vehicles and vehicle components for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol, dimethicone, and dimethicone copolyol; hydrocarbon-based materials such as petrolatum and squalane; and other vehicles and vehicle components that are suitable for administration to the skin, as well as mixtures of topical vehicle components as identified above or otherwise known to the art.

In one embodiment, the compositions of the present invention are oil-in-water emulsions. Liquids suitable for use in formulating compositions of the present invention include water, and water-miscible solvents such as glycols (e.g., ethylene glycol, butylene glycol, isoprene glycol, propylene glycol), glycerol, liquid polyols, dimethyl sulfoxide, and isopropyl alcohol. One or more aqueous vehicles may be present.

In one embodiment, formulations without methanol, ethanol, propanols, or butanols are desirable.

3. Surfactants and Emulsifiers

Many topical formulations contain chemical emulsions which use surface active ingredients (emulsifiers and surfactants) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures (droplets) that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, but are not limited to: cetyl alcohol, polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate (ceteth-10 is the polyethylene glycol ether of cetyl alcohol where n has an average value of 10; ceteth-10 phosphate is a mixture of phosphoric acid esters of ceteth-10), ceteth-20, Brij S10 (polyethylene glycol octadecyl ether, average $M_n$~711), and Poloxamers (including, but not limited to, Poloxamer 188 $(HO(C_2H_4O)_a(CH(CH_3)CH_2O)_b(C_2H_4O)_aH$, average molecular weight 8400) and Poloxamer 407 $(HO(C_2H_4O)_a(CH(CH_3)CH_2O)_b(C_2H_4O)_aH$, wherein a is about 101 and b is about 56)). Appropriate combinations or mixtures of such surfactants may also be used according to the present invention.

Many of these surfactants may also serve as emulsifiers in formulations of the present invention.

Other suitable emulsifiers for use in the formulations of the present invention include, but are not limited to, behentrimonium methosulfate-cetearyl alcohol, non-ionic emulsifiers like emulsifying wax, polyoxyethylene oleyl ether, PEG-40 stearate, cetostearyl alcohol (cetearyl alcohol), ceteareth-12, ceteareth-20, ceteareth-30, ceteareth alcohol, Ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, and PEG-100 stearate, ceramide 2, ceramide 3, stearic acid, cholesterol, steareth-2, and steareth-20, or combinations/mixtures thereof, as well as cationic emulsifiers like stearamidopropyl dimethylamine and behentrimonium methosulfate, or combinations/mixtures thereof 4. Moisturizers, Emollients, and Humectants One of the most important aspects of topical products in general, and cosmetic products in particular, is the consumer's perception of the aesthetic qualities of a product. For example, while white petrolatum is an excellent moisturizer and skin protectant, it is rarely used alone, especially on the face, because it is greasy, sticky, does not rub easily into the skin and may soil clothing. Consumers highly value products which are aesthetically elegant and have an acceptable tactile feel and performance on their skin.

Suitable moisturizers for use in the formulations of the present invention include, but are not limited to, lactic acid and other hydroxy acids and their salts, glycerol, propylene glycol, butylene glycol, sodium PCA, sodium hyaluronate, Carbowax 200, Carbowax 400, and Carbowax 800.

Suitable emollients or humectants for use in the formulations of the present invention include, but are not limited to, panthenol, cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, *Theobroma grandiflorum* seed butter, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, safflower oil, oleyl alcohol, oleic acid, stearic acid, dicaprylate/dicaprate, diethyl sebacate, isostearyl alcohol, pentylene glycol, isononyl isononanoate, and 1,3-bis(N-2-(hydroxyethyl)palmitoylamino)-2-hydroxypropane.

In addition, appropriate combinations and mixtures of any of these moisturizing agents and emollients may be used in accordance with the present invention.

5. Preservatives and Antioxidants

The composition may further include components adapted to improve the stability or effectiveness of the applied formulation.

Suitable preservatives for use in the present invention include, but are not limited to: ureas, such as imidazolidinyl urea and diazolidinyl urea; phenoxyethanol; sodium methyl paraben, methylparaben, ethylparaben, and propylparaben; potassium sorbate; sodium benzoate; sorbic acid; benzoic acid; formaldehyde; citric acid; sodium citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, sodium ascorbate/ascorbic acid, ascorbyl palmitate, propyl gallate, and chelating agents like EDTA (e.g., disodium EDTA), citric acid, and sodium citrate.

In certain embodiments, the antioxidant or preservative comprises (3-(4-chlorophenoxy)-2-hydroxypropyl)carbamate.

In certain embodiments, antioxidants or preservatives of the present invention may also function as a moisturizer or emollient, for example.

In addition, combinations or mixtures of these preservatives or anti-oxidants may also be used in the formulations of the present invention.

6. Active Agents

The active agent may be any material that has a desired effect when applied topically to a mammal, particularly a human. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones. Mixtures of any of these active agents may also be employed. Additionally, dermatologically-acceptable salts and esters of any of these agents may be employed.

6.1 Antibiotics

Representative antibiotics include, without limitation, benzoyl peroxide, alfa terpineol, octopirox, erythromycin, zinc, tetracyclin, triclosan, azelaic acid and its derivatives, phenoxy ethanol and phenoxy propanol, ethyl acetate, clindamycin (e.g., clindamycin phosphate) and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin. Mixtures of these antibiotic agents may also be employed. Additionally, dermatologically-acceptable salts and esters of any of these agents may be employed.

6.2 Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac, fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone; and niacinamide. Mixtures of these non-steroidal anti-inflammatory agents may also be employed, as well as the dermatologically acceptable salts and esters of these agents. For example, etofenamiate, a flufenamic acid derivative, is particularly useful for topical application.

6.3 Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters (including betamethasone dipropionate), chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

6.4 Anesthetics

Suitable anesthetics include the aminoacylanilide compounds such as lidocaine, prilocalne, bupivacaine, levo-bupivacaine, ropivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, butamben, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amide compounds such as dibucaine and related local anesthetic compounds; aminoketone compounds such as falicaine, dyclonine and related local anesthetic compounds; and amino ether compounds such as pramoxine, dimethisoquien, and related local anesthetic compounds; and para-amino benzoic acid esters such as benzocaine. Other suitable local anesthetics include ketocaine, dibucaine, amethocaine, propanacaine, and propipocaine.

6.5 Antimicrobial Agents

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin (e.g., clindamycin phosphate), ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, framesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, clindamycin phosphate, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

6.6 Keratolytic Agents

Suitable keratolytic agents include, but are not limited to, urea, salicylic acid, papain, sulfur, glycolic acid, pyruvic acid, resorcinol, N-acetylcysteine, retinoids such as retinoic acid (e.g., tretinoin) and its derivatives (e.g., cis and trans, esters), retinol, alpha hydroxy acids, beta hydroxy acids, coal tar, and combinations thereof.

7. Purging Gases

In one embodiment, the air in the container charged with the composition is replaced by an inert gas. In certain embodiments, the inert gas is selected from the group consisting of argon, nitrogen, and mixtures thereof.

8. Buffer Salts

Suitable buffer salts are well-known in the art. Examples of suitable buffer salts include, but are not limited to sodium citrate, citric acid, sodium phosphate monobasic, sodium phosphate dibasic, sodium phosphate tribasic, potassium phosphate monobasic, potassium phosphate dibasic, and potassium phosphate tribasic.

9. Viscosity Modifiers

Suitable viscosity adjusting agents (i.e., thickening and thinning agents or viscosity modifying agents) for use in the formulations of the present invention include, but are not limited to, protective colloids or non-ionic gums such as hydroxyethylcellulose, xanthan gum, and sclerotium gum, as well as magnesium aluminum silicate, silica, microcrystalline wax, beeswax, paraffin, and cetyl palmitate. In addition, appropriate combinations or mixtures of these viscosity adjusters may be utilized according to the present invention.

10. Additional Constituents

Additional constituents suitable for incorporation into the emulsions of the present invention include, but are not limited to: skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, antistatic agents, astringents (e.g., witch hazel, alcohol, and herbal extracts such as chamomile extract), binders/excipients, buffering agents, chelating agents, film forming agents, conditioning agents, opacifying agents, lipids, immunomodulators, and pH adjusters (e.g., citric acid, sodium hydroxide, and sodium phosphate).

For example, lipids normally found in healthy skin (or their functional equivalents) may be incorporated into the emulsions of the present invention. In certain embodiments, the lipid is selected from the group consisting of ceramides, cholesterol, and free fatty acids. Examples of lipids include, but are not limited to, ceramide 1, ceramide 2, ceramide 3, ceramide 4, ceramide 5, ceramide 6, hydroxypropyl bispalmitamide MEA, and hydroxypropyl bislauramide MEA, and combinations thereof.

Examples of peptides that interact with protein structures of the dermal-epidermal junction include palmitoyl dipeptide-5 diaminobutyloyl hydroxythreonine and palmitoyl dipeptide-6 diaminohydroxybutyrate.

Examples of skin soothing agents include, but are not limited to algae extract, mugwort extract, stearyl glycyrrhetinate, bisabolol, allantoin, aloe, avocado oil, green tea extract, hops extract, chamomile extract, colloidal oatmeal, calamine, cucumber extract, and combinations thereof.

In certain embodiments, the compositions comprise bergamot or bergamot oil. Bergamot oil is a natural skin toner and detoxifier. In certain embodiments, it may prevent premature aging of skin and may have excellent effects on oily skin conditions and acne.

Examples of vitamins include, but are not limited to, vitamins A, D, E, K, and combinations thereof. Vitamin analogues are also contemplated; for example the vitamin D analogues calcipotriene or calcipotriol.

In certain embodiments, the vitamin may be present as tetrahexyldecyl ascorbate. This compound exhibits anti-oxidant activity, inhibiting lipid peroxidation. In certain embodiments, use can mitigate the damaging effects of UV exposure. Studies have shown it to stimulate collagen production as well as clarifying and brightening the skin by inhibiting melanogenesis (the production of pigment) thereby promoting a more even skin tone.

Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof.

Suitable fragrances and colors may be used in the formulations of the present invention. Examples of fragrances and colors suitable for use in topical products are known in the art.

Suitable immunomodulators include, but are not limited to, tetrachlorodecaoxide, deoxycholic acid, tacrolimus, pimecrolimus, and beta-glucan.

In certain embodiments, palmitoyl-lysyl-valyl-lysine bistrifluoroacetate is added. This peptide stimulates collagen synthesis in human fibroblasts.

Often, one constituent of a composition may accomplish several functions. In one embodiment, the present invention relates to constituents that may act as a lubricant, an emollient, or a skin-penetrating agent. In one embodiment, the multi-functional constituent is socetyl stearate, isopropyl isostearate, isopropyl palmitate, or isopropyl myristate.

Exemplary Microemulsions of the Invention

In certain embodiments, the invention relates to a microemulsion, comprising: an aqueous phase; a first surfactant; and a second surfactant.

In certain embodiments, the invention relates to a microemulsion, consisting essentially of: an aqueous phase; a first surfactant; and a second surfactant.

In certain embodiments, the invention relates to a microemulsion, consisting of: an aqueous phase; a first surfactant; and a second surfactant.

In certain embodiments, the invention relates to any one of the aforementioned microemulsions, wherein the aqueous phase is present in an amount from about 75% to about 95% by weight of the microemulsion. In certain embodiments, the invention relates to any one of the aforementioned microemulsions, wherein the aqueous phase is present in about 75%, about 80%, about 85%, about 90%, or about 95% by weight of the microemulsion. In certain embodiments, the invention relates to any one of the aforementioned microemulsions, wherein the aqueous phase is present in about 80% by weight of the microemulsion. In certain embodiments, the invention relates to any one of the aforementioned microemulsions, wherein the aqueous phase is present in about 90% by weight of the microemulsion.

In certain embodiments, the invention relates to any one of the aforementioned microemulsions, wherein the aqueous phase is water.

In certain embodiments, the invention relates to any one of the aforementioned microemulsions, wherein the aqueous phase comprises water.

In certain embodiments, the invention relates to any one of the aforementioned microemulsions, wherein the aqueous phase comprises a moisturizer or emollient.

In certain embodiments, the moisturizer or emollient is selected from the group consisting of panthenol, petrolatum, lactic acid, glycerol, butylene glycol, sodium PCA, sodium hyaluronate, Carbowax 200, Carbowax 400, Carbowax 800, cetyl palmitate, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, dimethicone/divinyldimethicone/silsesquioxance cross polymer, polydimethylsiloxane, caprylic/capric triglyceride, shea butter, jojoba wax, sunflower wax, mimosa wax, phenyl trimethicone, cyclomethicone, $C_{12}$-$C_{15}$ alkyl benzoates, $C_{12}$-$C_{15}$ alkyl ethylhexanoates, dimethiconol, propylene glycol, *Theobroma grandiflorum* seed butter, ceramide 2, hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, safflower oil, oleyl alcohol, stearic acid, dicaprylate/dicaprate, diethyl sebacate, isostearyl alcohol, pentylene glycol, 1,3-bis(N-2-(hydroxyethyl)palmitoylamino)-2-hydroxypropane, hydrolyzed rice extract, cetyl alcohol, dipalmitoyl hydroxyproline, and combinations/mixtures thereof.

In certain embodiments, the moisturizer or emollient is selected from the group consisting of panthenol, allantoin, sodium hyaluraonate, pentylene glycol, and combinations/mixtures thereof.

In certain embodiments, the moisturizer or emollient is present in an amount from about 0.8% to about 2.3% by weight of the aqueous phase. In certain embodiments, the moisturizer or emollient is present in about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2% or about 2.3% by weight of the aqueous phase.

In certain embodiments, the moisturizer or emollient comprises panthenol; and the panthenol is present in an amount from about 0.5% to about 1.5% by weight of the aqueous phase. In certain embodiments, the panthenol is present in about 0.5%, about 0.6%, about 0.7%, about 0.8%, about 0.9%, about 1.0%, about 1.1%, about 1.2%, about 1.3%, about 1.4%, or about 1.5% by weight of the aqueous phase. In certain embodiments, the panthenol is present in about 1.0% by weight of the aqueous phase.

In certain embodiments, the moisturizer or emollient comprises allantoin; and the allantoin is present in an amount from about 0.2% to about 0.6% by weight of the aqueous phase. In certain embodiments, the allantoin is present in about 0.2%, about 0.3%, about 0.4%, about 0.5%, or about 0.6% by weight of the aqueous phase. In certain embodiments, the allantoin is present in about 0.4% by weight of the aqueous phase.

In certain embodiments, the moisturizer or emollient comprises sodium hyaluronate; and the sodium hyaluronate is present in an amount from about 0.005% to about 0.02% by weight of the aqueous phase. In certain embodiments, the sodium hyaluronate is present in about 0.005%, about 0.01%, about 0.015%, or about 0.02% by weight of the aqueous phase. In certain embodiments, the sodium hyaluronate is present in about 0.01% by weight of the aqueous phase.

In certain embodiments, the moisturizer or emollient comprises pentylene glycol; and the pentylene glycol is present in an amount from about 0.1% to about 0.3% by weight of the aqueous phase. In certain embodiments, the pentylene glycol is present in about 0.1%, about 0.2%, or about 0.3% by weight of the aqueous phase. In certain embodiments, the pentylene glycol is present in about 0.2% by weight of the aqueous phase.

In certain embodiments, the invention relates to any one of the aforementioned microemulsions, wherein the aqueous phase comprises an anti-inflammatory agent. In certain embodiments, the anti-inflammatory agent is niacinamide.

In certain embodiments, the anti-inflammatory agent is present in an amount from about 0.5% to about 2% by weight of the aqueous phase. In certain embodiments, the anti-inflammatory agent is present in about 0.5%, about 1%, about 1.5%, or about 2% by weight of the aqueous phase. In certain embodiments, the anti-inflammatory agent is present in about 1% by weight of the aqueous phase.

In certain embodiments, the invention relates to any one of the aforementioned microemulsions, wherein the aqueous phase comprises an antioxidant or preservative.

In certain embodiments, the antioxidant or preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid, sodium bisulfite, butylated hydroxytoluene, butylated hydroxyanisole, α-tocopherol, tocopheryl acetate, sodium ascorbate/ascorbic acid, ascorbyl palmitate, propyl gallate, disodium EDTA, citric acid, and sodium citrate, and combinations/mixtures thereof.

In certain embodiments, the antioxidant or preservative is selected from the group consisting of potassium sorbate, sodium benzoate, disodium EDTA, and combinations/mixtures thereof.

In certain embodiments, the antioxidant or preservative is present in an amount from about 0.2% to about 0.6% by weight of the aqueous phase.

In certain embodiments, the antioxidant or preservative comprises potassium sorbate; and the potassium sorbate is present in an amount from about 0.07% to about 0.23% by weight of the aqueous phase. In certain embodiments, the potassium sorbate is present in about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.21%, about 0.22% or about 0.23% by weight of the aqueous phase. In certain embodiments, the potassium sorbate is present in about 0.15% by weight of the aqueous phase.

In certain embodiments, the antioxidant or preservative comprises sodium benzoate; and the sodium benzoate is present in an amount from about 0.07% to about 0.23% by weight of the aqueous phase. In certain embodiments, the sodium benzoate is present in about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.21%, about 0.22% or about 0.23% by weight of the aqueous phase. In certain embodiments, the sodium benzoate is present in about 0.15% by weight of the aqueous phase.

In certain embodiments, the antioxidant or preservative comprises disodium EDTA; and the disodium EDTA is present in an amount from about 0.05% to about 0.15% by weight of the aqueous phase. In certain embodiments, the disodium EDTA is present in about 0.05%, about 0.06%, about 0.07%, about 0.08%, about 0.09%, about 0.10%, about 0.11%, about 0.12%, about 0.13%, about 0.14%, or about 0.15% by weight of the aqueous phase. In certain embodiments, the disodium EDTA is present in about 0.10% by weight of the aqueous phase.

In certain embodiments, the invention relates to any one of the aforementioned microemulsions, wherein the aqueous phase comprises a pH adjuster. In certain embodiments, the pH adjuster is sodium hydroxide.

In certain embodiments, the pH adjuster is present in an amount from about 0.02% to about 0.1% by weight of the aqueous phase. In certain embodiments, the pH adjuster is present in about 0.02%, about 0.04%, about 0.06%, about 0.08%, or about 0.1% by weight of the aqueous phase.

In certain embodiments, the invention relates to any one of the aforementioned microemulsions, wherein the first surfactant is present in an amount from about 1% to about 8% by weight of the microemulsion. In certain embodiments, the invention relates to any one of the aforementioned microemulsions, wherein the first surfactant is present in about 1%, about 2%, about 3%, about 4%, about 5%, about 6%, about 7%, or about 8% by weight of the microemulsion. In certain embodiments, the invention relates to any one of the aforementioned microemulsions, wherein the first surfactant is present in about 3% by weight of the microemulsion. In certain embodiments, the invention relates to any one of the aforementioned microemulsions, wherein the first surfactant is present in about 5% by weight of the microemulsion.

In certain embodiments, the invention relates to any one of the aforementioned microemulsions, wherein the first surfactant comprises a cyclodextrin or a derivative of a cyclodextrin. In certain embodiments, the invention relates to any one of the aforementioned microemulsions, wherein the first surfactant is a cyclodextrin or a derivative of a cyclodextrin. In certain embodiments, the invention relates to any one of the aforementioned microemulsions, wherein the first surfactant is a cyclodextrin. In certain embodiments, the invention relates to any one of the aforementioned microemulsions, wherein the first surfactant is hydroxypropyl α-cyclodextrin, hydroxypropyl β-cyclodextrin, or hydroxypropyl γ-cyclodextrin. In certain embodiments, the invention relates to any one of the aforementioned microemulsions, wherein the first surfactant is hydroxypropyl β-cyclodextrin.

In certain embodiments, the invention relates to any one of the aforementioned microemulsions, wherein the second surfactant is present in an amount from about 4% to about 22% by weight of the microemulsion. In certain embodiments, the invention relates to any one of the aforementioned microemulsions, wherein the second surfactant is present in about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, or about 22% by weight of the microemulsion. In certain embodiments, the invention relates to any one of the aforementioned microemulsions, wherein the second surfactant is present in about 7% by weight of the microemulsion. In certain embodiments, the invention relates to any one of the aforementioned microemulsions, wherein the second surfactant is present in about 15% by weight of the microemulsion.

In certain embodiments, the invention relates to any one of the aforementioned microemulsions, wherein the second surfactant comprises caprylocaproyl macrogol-8 glycerides or caprylocaproyl polyoxyl-8 glycerides. In certain embodiments, the invention relates to any one of the aforementioned microemulsions, wherein the second surfactant is caprylocaproyl macrogol-8 glycerides or caprylocaproyl polyoxyl-8 glycerides, or a combination thereof.

In certain embodiments, the invention relates to a microemulsion, comprising:
  water, in an amount of about 80% by weight of the microemulsion;
  hydroxypropyl β-cyclodextrin, in an amount of about 5% by weight of the microemulsion; and
  caprylocaproyl macrogol-8 glycerides or caprylocaproyl polyoxyl-8 glycerides, in an amount of about 15% by weight of the microemulsion.

In certain embodiments, the invention relates to a microemulsion, consisting essentially of:
  water, in an amount of about 80% by weight of the microemulsion;
  hydroxypropyl β-cyclodextrin, in an amount of about 5% by weight of the microemulsion; and
  caprylocaproyl macrogol-8 glycerides or caprylocaproyl polyoxyl-8 glycerides, in an amount of about 15% by weight of the microemulsion.

In certain embodiments, the invention relates to a microemulsion, consisting of:
  water, in an amount of about 80% by weight of the microemulsion;
  hydroxypropyl β-cyclodextrin, in an amount of about 5% by weight of the microemulsion; and
  caprylocaproyl macrogol-8 glycerides or caprylocaproyl polyoxyl-8 glycerides, in an amount of about 15% by weight of the microemulsion.

In certain embodiments, the invention relates to a microemulsion, comprising:
  water, in an amount of about 90% by weight of the microemulsion;
  hydroxypropyl β-cyclodextrin, in an amount of about 3% by weight of the microemulsion; and
  caprylocaproyl macrogol-8 glycerides or caprylocaproyl polyoxyl-8 glycerides, in an amount of about 7% by weight of the microemulsion.

In certain embodiments, the invention relates to a microemulsion, consisting essentially of:
  water, in an amount of about 90% by weight of the microemulsion;
  hydroxypropyl β-cyclodextrin, in an amount of about 3% by weight of the microemulsion; and
  caprylocaproyl macrogol-8 glycerides or caprylocaproyl polyoxyl-8 glycerides, in an amount of about 7% by weight of the microemulsion.

In certain embodiments, the invention relates to a microemulsion, consisting of:
  water, in an amount of about 90% by weight of the microemulsion;
  hydroxypropyl β-cyclodextrin, in an amount of about 3% by weight of the microemulsion; and
  caprylocaproyl macrogol-8 glycerides or caprylocaproyl polyoxyl-8 glycerides, in an amount of about 7% by weight of the microemulsion.

In certain embodiments, the invention relates to any one of the aforementioned microemulsions, wherein the microemulsion does not comprise methanol, ethanol, propanol, or butanol.

Exemplary Properties of Microemulsions of the Invention

In certain embodiments, the invention relates to any one of the aforementioned microemulsions, wherein the microemulsion is substantially optically clear.

In certain embodiments, the invention relates to any one of the aforementioned microemulsions, wherein the microemulsion is substantially stable at room temperature.

Exemplary Methods of Making Microemulsions

In certain embodiments, the invention relates to a method of making any one of the aforementioned microemulsions, comprising the step of combining the aqueous phase, the first surfactant, and the second surfactant.

Exemplary Micro emulsions Comprising Active Agents

In certain embodiments, the invention relates to an active agent-containing microemulsion, comprising: an aqueous phase; an active agent; a first surfactant; and a second surfactant.

In certain embodiments, the invention relates to an active agent-containing microemulsion, consisting essentially of: an aqueous phase; an active agent; a first surfactant; and a second surfactant.

In certain embodiments, the invention relates to an active agent-containing microemulsion, consisting of: an aqueous phase; an active agent; a first surfactant; and a second surfactant.

In certain embodiments, the invention relates to any one of the aforementioned active agent-containing microemulsions, wherein the active agent comprises retinol. In certain embodiments, the invention relates to any one of the aforementioned active agent-containing microemulsions, wherein the active agent is retinol.

In certain embodiments, the invention relates to any one of the aforementioned active agent-containing microemulsions, wherein the active agent-containing microemulsion comprises any one of the aforementioned microemulsions; and an active agent.

In certain embodiments, the invention relates to any one of the aforementioned active agent-containing microemulsions, wherein the active agent is present in an amount from about 0.01% to about 5% by weight of the active agent-containing microemulsion. In certain embodiments, the invention relates to any one of the aforementioned active agent-containing microemulsions, wherein the active agent is present in about 0.01%, about 0.02%, about 0.04%, about 0.06%, about 0.08%, about 0.1%, about 0.2%, about 0.3%, about 0.4%, about 0.5%, about 0.6%, about 0.7%, about 0.8%, about 0.9%, about 1.0%, about 1.2%, about 1.4%, about 1.6%, about 1.8%, about 2.0%, about 2.2%, about 2.4%, about 2.6%, about 2.8%, about 3.0%, about 3.5%, about 4.0%, about 4.5%, or about 5.0% by weight of the active agent-containing microemulsion. In certain embodiments, the invention relates to any one of the aforementioned active agent-containing microemulsions, wherein the active agent is present in about 0.06% by weight of the active agent-containing microemulsion. In certain embodiments, the invention relates to any one of the aforementioned active agent-containing microemulsions, wherein the active agent is present in about 1.2% by weight of the active agent-containing microemulsion.

Exemplary Properties of Active Agent-Containing Microemulsions of the Invention

In certain embodiments, the invention relates to any one of the aforementioned active agent-containing microemulsions, wherein the active agent-containing microemulsion is substantially optically clear.

In certain embodiments, the invention relates to any one of the aforementioned active agent-containing microemulsions, wherein the active agent-containing microemulsion is substantially stable at room temperature.

Exemplary Methods of Making Microemulsions

In certain embodiments, the invention relates to a method of making any one of the aforementioned active agent-containing microemulsions, comprising the step of combining the aqueous phase, the first surfactant, the second surfactant, and the active agent.

Exemplary Formulations of the Invention

In certain embodiments, the invention relates to a formulation comprising any one of the aforementioned microemulsions; an active agent; a moisturizer or emollient; a third surfactant; an antioxidant or preservative; a viscosity modifying agent; and a pH adjuster.

In certain embodiments, the invention relates to a formulation, comprising:

any one of the aforementioned microemulsions, in an amount from about 28% to about 84% by weight of the formulation;

retinol, from about 0.08% to about 2.5% by weight of the formulation;

isononyl isononanoate, from about 2% to about 9% by weight of the formulation;

cetyl alcohol, glyceryl stearate, PEG-75 stearate, ceteth-20, and steareth-20, taken together, from about 2.5% to about 7.5% by weight of the formulation;

pentylene glycol, from about 0.1% to about 0.4% by weight of the formulation;

$C_{12}$-$C_{15}$ alkyl ethylhexanoates, from about 1% to about 6% by weight of the formulation;

Palmitoyl-lysyl-valyl-lysine bistrifluoroacetate and glycerin, taken together, from about 1% to about 5% by weight of the formulation;

Jojoba wax, sunflower wax, and mimosa wax, taken together, from about 1% to about 3% by weight of the formulation;

Shea butter, from about 1% to about 3% by weight of the formulation;

Caprylic/capric triglyceride, from about 1% to about 3% by weight of the formulation;

Polydimethylsiloxane, from about 1% to about 3% by weight of the formulation;

Dimethicone/divinyldimethicone/silsesquioxane cross polymer, from about 1% to about 3% by weight of the formulation;

Dipalmitoyl hydroxyproline, from about 0.5% to about 1.5% by weight of the formulation;

Cetyl alcohol, from about 0.5% to about 2.2% by weight of the formulation;

Sodium hyaluronate, from about 0.005% to about 0.02% by weight of the formulation;

Panthenol, from about 0.5% to about 1.5% by weight of the formulation;

Niacinamide, from about 0.5% to about 1.5% by weight of the formulation;

Butylene glycol and hydrolyzed rice extract, taken together, from about 0.5% to about 1.5% by weight of the formulation;

Algae extract and mugwort extract, taken together, from about 0.5% to about 1.5% by weight of the formulation;
Glycerin, palmitoyl dipeptide-5 diaminobutyloyl hydroxythreonine, and palmitoyl dipeptide-6 diaminohydroxybutyrate, taken together, from about 0.5% to about 1.5% by weight of the formulation;
Magnesium aluminum silicate, from about 0.3% to about 2.2% by weight of the formulation;
Tocopheryl acetate, from about 0.25% to about 0.75% by weight of the formulation;
Tetrahexyldecyl ascorbate, from about 0.25% to about 0.75% by weight of the formulation;
Allantoin, from about 0.2% to about 0.6% by weight of the formulation;
Bergamot, from about 0.15% to about 0.45% by weight of the formulation;
(3-(4-chlorophenoxy)-2-hydroxypropyl)carbamate, from about 0.15% to about 0.45% by weight of the formulation;
Sodium ascorbate, from about 0.1% to about 0.4% by weight of the formulation;
Bisabolol, from about 0.1% to about 0.3% by weight of the formulation;
Tocopherol, from about 0.05% to about 0.25% by weight of the formulation;
Potassium sorbate, from about 0.05% to about 0.25% by weight of the formulation;
Sodium benzoate, from about 0.05% to about 0.25% by weight of the formulation;
Butylated hydroxytoluene, from about 0.05% to about 0.15% by weight of the formulation;
Stearyl glycyrrhetinate, from about 0.05% to about 0.15% by weight of the formulation;
Xanthan gum, from about 0.05% to about 0.3% by weight of the formulation;
Disodium EDTA, from about 0.05% to about 0.15% by weight of the formulation; and
Sodium hydroxide, from about 0.02% to about 0.06% by weight of the formulation,
wherein the sum of the amounts of the components is less than or equal to 100%.

In certain embodiments, the invention relates to a formulation, consisting essentially of:
any one of the aforementioned microemulsions, in an amount from about 28% to about 84% by weight of the formulation;
retinol, from about 0.08% to about 2.5% by weight of the formulation;
isononyl isononanoate, from about 2% to about 9% by weight of the formulation;
cetyl alcohol, glyceryl stearate, PEG-75 stearate, ceteth-20, and steareth-20, taken together, from about 2.5% to about 7.5% by weight of the formulation;
pentylene glycol, from about 0.1% to about 0.4% by weight of the formulation;
$C_{12}$-$C_{15}$ alkyl ethylhexanoates, from about 1% to about 6% by weight of the formulation;
Palmitoyl-lysyl-valyl-lysine bistrifluoroacetate and glycerin, taken together, from about 1% to about 5% by weight of the formulation;
Jojoba wax, sunflower wax, and mimosa wax, taken together, from about 1% to about 3% by weight of the formulation;
Shea butter, from about 1% to about 3% by weight of the formulation; Caprylic/capric triglyceride, from about 1% to about 3% by weight of the formulation;
Polydimethylsiloxane, from about 1% to about 3% by weight of the formulation;
Dimethicone/divinyldimethicone/silsesquioxane cross polymer, from about 1% to about 3% by weight of the formulation;
Dipalmitoyl hydroxyproline, from about 0.5% to about 1.5% by weight of the formulation;
Cetyl alcohol, from about 0.5% to about 2.2% by weight of the formulation;
Sodium hyaluronate, from about 0.005% to about 0.02% by weight of the formulation;
Panthenol, from about 0.5% to about 1.5% by weight of the formulation;
Niacinamide, from about 0.5% to about 1.5% by weight of the formulation;
Butylene glycol and hydrolyzed rice extract, taken together, from about 0.5% to about 1.5% by weight of the formulation;
Algae extract and mugwort extract, taken together, from about 0.5% to about 1.5% by weight of the formulation;
Glycerin, palmitoyl dipeptide-5 diaminobutyloyl hydroxythreonine, and palmitoyl dipeptide-6 diaminohydroxybutyrate, taken together, from about 0.5% to about 1.5% by weight of the formulation;
Magnesium aluminum silicate, from about 0.3% to about 2.2% by weight of the formulation;
Tocopheryl acetate, from about 0.25% to about 0.75% by weight of the formulation;
Tetrahexyldecyl ascorbate, from about 0.25% to about 0.75% by weight of the formulation;
Allantoin, from about 0.2% to about 0.6% by weight of the formulation;
Bergamot, from about 0.15% to about 0.45% by weight of the formulation;
(3-(4-chlorophenoxy)-2-hydroxypropyl)carbamate, from about 0.15% to about 0.45% by weight of the formulation;
Sodium ascorbate, from about 0.1% to about 0.4% by weight of the formulation;
Bisabolol, from about 0.1% to about 0.3% by weight of the formulation;
Tocopherol, from about 0.05% to about 0.25% by weight of the formulation;
Potassium sorbate, from about 0.05% to about 0.25% by weight of the formulation;
Sodium benzoate, from about 0.05% to about 0.25% by weight of the formulation;
Butylated hydroxytoluene, from about 0.05% to about 0.15% by weight of the formulation;
Stearyl glycyrrhetinate, from about 0.05% to about 0.15% by weight of the formulation;
Xanthan gum, from about 0.05% to about 0.3% by weight of the formulation;
Disodium EDTA, from about 0.05% to about 0.15% by weight of the formulation; and
Sodium hydroxide, from about 0.02% to about 0.06% by weight of the formulation,
wherein the sum of the amounts of the components is less than or equal to 100%.

In certain embodiments, the invention relates to a formulation, consisting of:
any one of the aforementioned microemulsions, in an amount from about 28% to about 84% by weight of the formulation;
retinol, from about 0.08% to about 2.5% by weight of the formulation;

isononyl isononanoate, from about 2% to about 9% by weight of the formulation;
cetyl alcohol, glyceryl stearate, PEG-75 stearate, ceteth-20, and steareth-20, taken together, from about 2.5% to about 7.5% by weight of the formulation;
pentylene glycol, from about 0.1% to about 0.4% by weight of the formulation;
$C_{12}$-$C_{15}$ alkyl ethylhexanoates, from about 1% to about 6% by weight of the formulation;
Palmitoyl-lysyl-valyl-lysine bistrifluoroacetate and glycerin, taken together, from about 1% to about 5% by weight of the formulation;
Jojoba wax, sunflower wax, and mimosa wax, taken together, from about 1% to about 3% by weight of the formulation;
Shea butter, from about 1% to about 3% by weight of the formulation;
Caprylic/capric triglyceride, from about 1% to about 3% by weight of the formulation;
Polydimethylsiloxane, from about 1% to about 3% by weight of the formulation;
Dimethicone/divinyldimethicone/silsesquioxane cross polymer, from about 1% to about 3% by weight of the formulation;
Dipalmitoyl hydroxyproline, from about 0.5% to about 1.5% by weight of the formulation;
Cetyl alcohol, from about 0.5% to about 2.2% by weight of the formulation;
Sodium hyaluronate, from about 0.005% to about 0.02% by weight of the formulation;
Panthenol, from about 0.5% to about 1.5% by weight of the formulation;
Niacinamide, from about 0.5% to about 1.5% by weight of the formulation;
Butylene glycol and hydrolyzed rice extract, taken together, from about 0.5% to about 1.5% by weight of the formulation;
Algae extract and mugwort extract, taken together, from about 0.5% to about 1.5% by weight of the formulation;
Glycerin, palmitoyl dipeptide-5 diaminobutyloyl hydroxythreonine, and palmitoyl dipeptide-6 diaminohydroxybutyrate, taken together, from about 0.5% to about 1.5% by weight of the formulation;
Magnesium aluminum silicate, from about 0.3% to about 2.2% by weight of the formulation;
Tocopheryl acetate, from about 0.25% to about 0.75% by weight of the formulation;
Tetrahexyldecyl ascorbate, from about 0.25% to about 0.75% by weight of the formulation;
Allantoin, from about 0.2% to about 0.6% by weight of the formulation;
Bergamot, from about 0.15% to about 0.45% by weight of the formulation;
(3-(4-chlorophenoxy)-2-hydroxypropyl)carbamate, from about 0.15% to about 0.45% by weight of the formulation;
Sodium ascorbate, from about 0.1% to about 0.4% by weight of the formulation;
Bisabolol, from about 0.1% to about 0.3% by weight of the formulation;
Tocopherol, from about 0.05% to about 0.25% by weight of the formulation;
Potassium sorbate, from about 0.05% to about 0.25% by weight of the formulation;
Sodium benzoate, from about 0.05% to about 0.25% by weight of the formulation;
Butylated hydroxytoluene, from about 0.05% to about 0.15% by weight of the formulation;
Stearyl glycyrrhetinate, from about 0.05% to about 0.15% by weight of the formulation;
Xanthan gum, from about 0.05% to about 0.3% by weight of the formulation;
Disodium EDTA, from about 0.05% to about 0.15% by weight of the formulation; and
Sodium hydroxide, from about 0.02% to about 0.06% by weight of the formulation,
wherein the sum of the amounts of the components is equal to 100%.

In certain embodiments, the invention relates to a formulation, comprising:
any one of the aforementioned microemulsions, in about 55.19% by weight of the formulation;
retinol, in about 1.33% by weight of the formulation;
isononyl isononanoate, in about 6.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 4.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 0.60% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;

Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, consisting essentially of:
any one of the aforementioned microemulsions, in about 55.19% by weight of the formulation;
retinol, in about 1.33% by weight of the formulation;
isononyl isononanoate, in about 6.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 4.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 0.60% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, consisting of:
any one of the aforementioned microemulsions, in about 55.19% by weight of the formulation;
retinol, in about 1.33% by weight of the formulation;
isononyl isononanoate, in about 6.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 4.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation; Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 0.60% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;

(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, comprising:
any one of the aforementioned microemulsions, in about 54.92% by weight of the formulation;
retinol, in about 1.20% by weight of the formulation;
isononyl isononanoate, in about 6.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 4.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.00% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, consisting essentially of:
any one of the aforementioned microemulsions, in about 54.92% by weight of the formulation;
retinol, in about 1.20% by weight of the formulation;
isononyl isononanoate, in about 6.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 4.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;

Magnesium aluminum silicate, in about 1.00% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, consisting of:
any one of the aforementioned microemulsions, in about 54.92% by weight of the formulation;
retinol, in about 1.20% by weight of the formulation;
isononyl isononanoate, in about 6.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 4.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.00% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, comprising:
any one of the aforementioned microemulsions, in about 55.94% by weight of the formulation;
retinol, in about 0.18% by weight of the formulation;
isononyl isononanoate, in about 6.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 4.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;

Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.00% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, consisting essentially of:
 any one of the aforementioned microemulsions, in about 55.94% by weight of the formulation;
 retinol, in about 0.18% by weight of the formulation;
 isononyl isononanoate, in about 6.00% by weight of the formulation;
 cetyl alcohol, glyceryl stearate, PEG-75 stearate, ceteth-20, and steareth-20, taken together, in about 5.00% by weight of the formulation;
 pentylene glycol, in about 0.25% by weight of the formulation;
 $C_{12}$-$C_{15}$ alkyl ethylhexanoates, in about 4.00% by weight of the formulation;
 Palmitoyl-lysyl-valyl-lysine bistrifluoroacetate and glycerin, taken together, in about 2.50% by weight of the formulation;
 Jojoba wax, sunflower wax, and mimosa wax, taken together, in about 2.00% by weight of the formulation;
 Shea butter, in about 2.00% by weight of the formulation;
 Caprylic/capric triglyceride, in about 2.00% by weight of the formulation;
 Polydimethylsiloxane, in about 1.50% by weight of the formulation;
 Dimethicone/divinyldimethicone/silsesquioxane cross polymer, in about 1.50% by weight of the formulation;
 Dipalmitoyl hydroxyproline, in about 1.00% by weight of the formulation;
 Cetyl alcohol, in about 1.00% by weight of the formulation;
 Sodium hyaluronate, in about 0.01% by weight of the formulation;
 Panthenol, in about 1.00% by weight of the formulation;
 Niacinamide, in about 1.00% by weight of the formulation;
 Butylene glycol and hydrolyzed rice extract, taken together, in about 1.00% by weight of the formulation;
 Algae extract and mugwort extract, taken together, in about 1.00% by weight of the formulation;
 Glycerin, palmitoyl dipeptide-5 diaminobutyloyl hydroxythreonine, and palmitoyl dipeptide-6 diaminohydroxybutyrate, taken together, in about 1.00% by weight of the formulation;
 Magnesium aluminum silicate, in about 1.00% by weight of the formulation;
 Tocopheryl acetate, in about 0.50% by weight of the formulation;
 Tetrahexyldecyl ascorbate, in about 0.50% by weight of the formulation;
 Allantoin, in about 0.40% by weight of the formulation;
 Bergamot, in about 0.30% by weight of the formulation;
 (3-(4-chlorophenoxy)-2-hydroxypropyl)carbamate, in about 0.30% by weight of the formulation;
 Sodium ascorbate, in about 0.24% by weight of the formulation;
 Bisabolol, in about 0.20% by weight of the formulation;
 Tocopherol, in about 0.16% by weight of the formulation;
 Potassium sorbate, in about 0.15% by weight of the formulation;
 Sodium benzoate, in about 0.15% by weight of the formulation;
 Butylated hydroxytoluene, in about 0.10% by weight of the formulation;
 Stearyl glycyrrhetinate, in about 0.10% by weight of the formulation;
 Xanthan gum, in about 0.10% by weight of the formulation;
 Disodium EDTA, in about 0.10% by weight of the formulation; and
 Sodium hydroxide, in about 0.04% by weight of the formulation.

In certain embodiments, the invention relates to a formulation, consisting of:
 any one of the aforementioned microemulsions, in about 55.94% by weight of the formulation;
 retinol, in about 0.18% by weight of the formulation;
 isononyl isononanoate, in about 6.00% by weight of the formulation;
 cetyl alcohol, glyceryl stearate, PEG-75 stearate, ceteth-20, and steareth-20, taken together, in about 5.00% by weight of the formulation;
 pentylene glycol, in about 0.25% by weight of the formulation;
 $C_{12}$-$C_{15}$ alkyl ethylhexanoates, in about 4.00% by weight of the formulation;
 Palmitoyl-lysyl-valyl-lysine bistrifluoroacetate and glycerin, taken together, in about 2.50% by weight of the formulation;
 Jojoba wax, sunflower wax, and mimosa wax, taken together, in about 2.00% by weight of the formulation;
 Shea butter, in about 2.00% by weight of the formulation;
 Caprylic/capric triglyceride, in about 2.00% by weight of the formulation;
 Polydimethylsiloxane, in about 1.50% by weight of the formulation;
 Dimethicone/divinyldimethicone/silsesquioxane cross polymer, in about 1.50% by weight of the formulation;

Dipalmitoyl hydroxyproline, in about 1.00% by weight of the formulation;
Cetyl alcohol, in about 1.00% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.00% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.10% by weight of the formulation;
Disodium EDTA, in about 0.10% by weight of the formulation; and
Sodium hydroxide, in about 0.04% by weight of the formulation.

In certain embodiments, the invention relates to a formulation, comprising:
any one of the aforementioned microemulsions, in about 57.82% by weight of the formulation;
retinol, in about 1.20% by weight of the formulation;
isononyl isononanoate, in about 4.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 2.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.50% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.50% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.20% by weight of the formulation;
Disodium EDTA, in about 0.10% by weight of the formulation; and
Sodium hydroxide, in about 0.04% by weight of the formulation.

In certain embodiments, the invention relates to a formulation, consisting essentially of:
any one of the aforementioned microemulsions, in about 57.82% by weight of the formulation;
retinol, in about 1.20% by weight of the formulation;
isononyl isononanoate, in about 4.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 2.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;

Shea butter, in about 2.00% by weight of the formulation;

Caprylic/capric triglyceride, in about 2.00% by weight of the formulation;

Polydimethylsiloxane, in about 1.50% by weight of the formulation;

Dimethicone/divinyldimethicone/silsesquioxane cross polymer, in about 1.50% by weight of the formulation;

Dipalmitoyl hydroxyproline, in about 1.00% by weight of the formulation;

Cetyl alcohol, in about 1.50% by weight of the formulation;

Sodium hyaluronate, in about 0.01% by weight of the formulation;

Panthenol, in about 1.00% by weight of the formulation;

Niacinamide, in about 1.00% by weight of the formulation;

Butylene glycol and hydrolyzed rice extract, taken together, in about 1.00% by weight of the formulation;

Algae extract and mugwort extract, taken together, in about 1.00% by weight of the formulation;

Glycerin, palmitoyl dipeptide-5 diaminobutyloyl hydroxythreonine, and palmitoyl dipeptide-6 diaminohydroxybutyrate, taken together, in about 1.00% by weight of the formulation;

Magnesium aluminum silicate, in about 1.50% by weight of the formulation;

Tocopheryl acetate, in about 0.50% by weight of the formulation;

Tetrahexyldecyl ascorbate, in about 0.50% by weight of the formulation;

Allantoin, in about 0.40% by weight of the formulation;

Bergamot, in about 0.30% by weight of the formulation;

(3-(4-chlorophenoxy)-2-hydroxypropyl)carbamate, in about 0.30% by weight of the formulation;

Sodium ascorbate, in about 0.24% by weight of the formulation;

Bisabolol, in about 0.20% by weight of the formulation;

Tocopherol, in about 0.16% by weight of the formulation;

Potassium sorbate, in about 0.15% by weight of the formulation;

Sodium benzoate, in about 0.15% by weight of the formulation;

Butylated hydroxytoluene, in about 0.10% by weight of the formulation;

Stearyl glycyrrhetinate, in about 0.10% by weight of the formulation;

Xanthan gum, in about 0.20% by weight of the formulation;

Disodium EDTA, in about 0.10% by weight of the formulation; and

Sodium hydroxide, in about 0.04% by weight of the formulation.

In certain embodiments, the invention relates to a formulation, consisting of:

any one of the aforementioned microemulsions, in about 57.82% by weight of the formulation;

retinol, in about 1.20% by weight of the formulation;

isononyl isononanoate, in about 4.00% by weight of the formulation;

cetyl alcohol, glyceryl stearate, PEG-75 stearate, ceteth-20, and steareth-20, taken together, in about 5.00% by weight of the formulation;

pentylene glycol, in about 0.25% by weight of the formulation;

$C_{12}$-$C_{15}$ alkyl ethylhexanoates, in about 2.00% by weight of the formulation;

Palmitoyl-lysyl-valyl-lysine bistrifluoroacetate and glycerin, taken together, in about 2.50% by weight of the formulation;

Jojoba wax, sunflower wax, and mimosa wax, taken together, in about 2.00% by weight of the formulation;

Shea butter, in about 2.00% by weight of the formulation;

Caprylic/capric triglyceride, in about 2.00% by weight of the formulation;

Polydimethylsiloxane, in about 1.50% by weight of the formulation;

Dimethicone/divinyldimethicone/silsesquioxane cross polymer, in about 1.50% by weight of the formulation;

Dipalmitoyl hydroxyproline, in about 1.00% by weight of the formulation;

Cetyl alcohol, in about 1.50% by weight of the formulation;

Sodium hyaluronate, in about 0.01% by weight of the formulation;

Panthenol, in about 1.00% by weight of the formulation;

Niacinamide, in about 1.00% by weight of the formulation;

Butylene glycol and hydrolyzed rice extract, taken together, in about 1.00% by weight of the formulation;

Algae extract and mugwort extract, taken together, in about 1.00% by weight of the formulation;

Glycerin, palmitoyl dipeptide-5 diaminobutyloyl hydroxythreonine, and palmitoyl dipeptide-6 diaminohydroxybutyrate, taken together, in about 1.00% by weight of the formulation;

Magnesium aluminum silicate, in about 1.50% by weight of the formulation;

Tocopheryl acetate, in about 0.50% by weight of the formulation;

Tetrahexyldecyl ascorbate, in about 0.50% by weight of the formulation;

Allantoin, in about 0.40% by weight of the formulation;

Bergamot, in about 0.30% by weight of the formulation;

(3-(4-chlorophenoxy)-2-hydroxypropyl)carbamate, in about 0.30% by weight of the formulation;

Sodium ascorbate, in about 0.24% by weight of the formulation;

Bisabolol, in about 0.20% by weight of the formulation;

Tocopherol, in about 0.16% by weight of the formulation;

Potassium sorbate, in about 0.15% by weight of the formulation;

Sodium benzoate, in about 0.15% by weight of the formulation;

Butylated hydroxytoluene, in about 0.10% by weight of the formulation;

Stearyl glycyrrhetinate, in about 0.10% by weight of the formulation;

Xanthan gum, in about 0.20% by weight of the formulation;

Disodium EDTA, in about 0.10% by weight of the formulation; and

Sodium hydroxide, in about 0.04% by weight of the formulation.

In certain embodiments, the invention relates to a formulation, comprising:

any one of the aforementioned microemulsions, in about 58.84% by weight of the formulation;

retinol, in about 0.18% by weight of the formulation;

isononyl isononanoate, in about 4.00% by weight of the formulation;

cetyl alcohol, glyceryl stearate, PEG-75 stearate, ceteth-20, and steareth-20, taken together, in about 5.00% by weight of the formulation;

pentylene glycol, in about 0.25% by weight of the formulation;
$C_{12}$-$C_{15}$ alkyl ethylhexanoates, in about 2.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.50% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.50% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.20% by weight of the formulation;
Disodium EDTA, in about 0.10% by weight of the formulation; and
Sodium hydroxide, in about 0.04% by weight of the formulation.

In certain embodiments, the invention relates to a formulation, consisting essentially of:
any one of the aforementioned microemulsions, in about 58.84% by weight of the formulation;
retinol, in about 0.18% by weight of the formulation;
isononyl isononanoate, in about 4.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 2.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.50% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.50% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.20% by weight of the formulation;
Disodium EDTA, in about 0.10% by weight of the formulation; and
Sodium hydroxide, in about 0.04% by weight of the formulation.

In certain embodiments, the invention relates to a formulation, consisting of:
any one of the aforementioned microemulsions, in about 58.84% by weight of the formulation;

retinol, in about 0.18% by weight of the formulation;
isononyl isononanoate, in about 4.00% by weight of the formulation;
cetyl alcohol, glyceryl stearate, PEG-75 stearate, ceteth-20, and steareth-20, taken together, in about 5.00% by weight of the formulation;
pentylene glycol, in about 0.25% by weight of the formulation;
$C_{12}$-$C_{15}$ alkyl ethylhexanoates, in about 2.00% by weight of the formulation;
Palmitoyl-lysyl-valyl-lysine bistrifluoroacetate and glycerin, taken together, in about 2.50% by weight of the formulation;
Jojoba wax, sunflower wax, and mimosa wax, taken together, in about 2.00% by weight of the formulation;
Shea butter, in about 2.00% by weight of the formulation;
Caprylic/capric triglyceride, in about 2.00% by weight of the formulation;
Polydimethylsiloxane, in about 1.50% by weight of the formulation;
Dimethicone/divinyldimethicone/silsesquioxane cross polymer, in about 1.50% by weight of the formulation;
Dipalmitoyl hydroxyproline, in about 1.00% by weight of the formulation;
Cetyl alcohol, in about 1.50% by weight of the formulation;
Sodium hyaluronate, in about 0.01% by weight of the formulation;
Panthenol, in about 1.00% by weight of the formulation;
Niacinamide, in about 1.00% by weight of the formulation;
Butylene glycol and hydrolyzed rice extract, taken together, in about 1.00% by weight of the formulation;
Algae extract and mugwort extract, taken together, in about 1.00% by weight of the formulation;
Glycerin, palmitoyl dipeptide-5 diaminobutyloyl hydroxythreonine, and palmitoyl dipeptide-6 diaminohydroxybutyrate, taken together, in about 1.00% by weight of the formulation;
Magnesium aluminum silicate, in about 1.50% by weight of the formulation;
Tocopheryl acetate, in about 0.50% by weight of the formulation;
Tetrahexyldecyl ascorbate, in about 0.50% by weight of the formulation;
Allantoin, in about 0.40% by weight of the formulation;
Bergamot, in about 0.30% by weight of the formulation;
(3-(4-chlorophenoxy)-2-hydroxypropyl)carbamate, in about 0.30% by weight of the formulation;
Sodium ascorbate, in about 0.24% by weight of the formulation;
Bisabolol, in about 0.20% by weight of the formulation;
Tocopherol, in about 0.16% by weight of the formulation;
Potassium sorbate, in about 0.15% by weight of the formulation;
Sodium benzoate, in about 0.15% by weight of the formulation;
Butylated hydroxytoluene, in about 0.10% by weight of the formulation;
Stearyl glycyrrhetinate, in about 0.10% by weight of the formulation;
Xanthan gum, in about 0.20% by weight of the formulation;
Disodium EDTA, in about 0.10% by weight of the formulation; and
Sodium hydroxide, in about 0.04% by weight of the formulation.

Exemplary Components of the Formulation

As outlined above, in certain embodiments, the invention relates to a formulation. The components described below may be present in any one of the aforementioned formulations.

In certain embodiments, the invention relates to any one of the aforementioned formulations, wherein the active agent is selected from the group consisting of salicylic acid, papain, sulfur, glycolic acid, pyruvic acid, resorcinol, N-acetylcysteine, retinoids such as retinoic acid (e.g., tretinoin) and its derivatives (e.g., cis and trans isomers, esters), retinol, alpha hydroxy acids, beta hydroxy acids, coal tar, and combinations thereof.

In certain embodiments, the invention relates to any one of the aforementioned formulations, wherein the active agent is retinol.

In certain embodiments, the invention relates to any one of the aforementioned formulations, wherein the retinol is stabilized by the microemulsion. In certain embodiments, the invention relates to any one of the aforementioned formulations, wherein the retinol is encapsulated in the microemulsion.

In certain embodiments, the invention relates to any one of the aforementioned formulations, wherein the active agent is substantially water insoluble.

In certain embodiments, the invention relates to any one of the aforementioned formulations wherein the active agent is present in an amount from about 0.01% to about 5% by weight of the formulation. In certain embodiments, the invention relates to any one of the aforementioned formulations, wherein the active agent is present in about 0.01%, about 0.02%, about 0.04%, about 0.06%, about 0.08%, about 0.1%, about 0.2%, about 0.3%, about 0.4%, about 0.5%, about 0.6%, about 0.7%, about 0.8%, about 0.9%, about 1.0%, about 1.2%, about 1.4%, about 1.6%, about 1.8%, about 2.0%, about 2.2%, about 2.4%, about 2.6%, about 2.8%, about 3.0%, about 3.5%, about 4.0%, about 4.5%, or about 5.0% by weight of the formulation.

In certain embodiments, the invention relates to any one of the aforementioned formulations, wherein the active agent is present in about 0.06% by weight of the formulation. In certain embodiments, the invention relates to any one of the aforementioned formulations, wherein the active agent is present in about 1.2% by weight of the formulation.

In certain embodiments, the invention relates to any one of the aforementioned formulations wherein retinol is present in an amount from about 0.01% to about 5% by weight of the formulation. In certain embodiments, the invention relates to any one of the aforementioned formulations, wherein retinol is present in about 0.01%, about 0.02%, about 0.04%, about 0.06%, about 0.08%, about 0.1%, about 0.2%, about 0.3%, about 0.4%, about 0.5%, about 0.6%, about 0.7%, about 0.8%, about 0.9%, about 1.0%, about 1.2%, about 1.4%, about 1.6%, about 1.8%, about 2.0%, about 2.2%, about 2.4%, about 2.6%, about 2.8%, about 3.0%, about 3.5%, about 4.0%, about 4.5%, or about 5.0% by weight of the formulation. In certain embodiments, the invention relates to any one of the aforementioned formulations, wherein retinol is present in about 0.06% by weight of the formulation. In certain embodiments, the invention relates to any one of the aforementioned formulations, wherein retinol is present in about 1.2% by weight of the formulation.

In certain embodiments, the invention relates to any one of the aforementioned formulations, wherein the third surfactant is selected from the group consisting of: cetyl alcohol, Polysorbate 20, Polysorbate 40, Polysorbate 60, Polysorbate 80, steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate (ceteth-10 is the polyethylene glycol ether of cetyl alcohol where n has an average value of 10; ceteth-10 phosphate is a mixture of phosphoric acid esters of ceteth-10), ceteth-20, Brij S10 (polyethylene glycol octadecyl ether, average $M_n$~711), Poloxamers (including, but not limited to, Poloxamer 188 ($HO(C_2H_4O)_a(CH(CH_3)CH_2O)_b(C_2H_4O)_aH$, average molecular weight 8400) and Poloxamer 407 ($HO(C_2H_4O)_a(CH(CH_3)CH_2O)_b(C_2H_4O)_aH$, wherein a is about 101 and b is about 56)), behentrimonium methosulfate-cetearyl alcohol, emulsifying wax, polyoxyethylene oleyl ether, PEG-40 stearate, cetostearyl alcohol (cetearyl alcohol), ceteareth-12, ceteareth-20, ceteareth-30, ceteareth alcohol, ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, PEG-100 stearate, ceramide 2, ceramide 3, stearic acid, cholesterol, steareth-2, steareth-20, stearamidopropyl dimethylamine, and behentrimonium methosulfate, and combinations/mixtures thereof.

In certain embodiments, the invention relates to any one of the aforementioned formulations, wherein the third surfactant is selected from the group consisting of: cetyl alcohol, Ceteth-20 (Ceteth-20 is the polyethylene glycol ether of cetyl alcohol where n has an average value of 20), PEG-75 stearate, glyceryl stearate, steareth-20, and combinations/mixtures thereof.

In certain embodiments, the invention relates to any one of the aforementioned formulations, wherein the third surfactant is present in an amount from about 2.5% to about 7.5% by weight of the formulation. In certain embodiments, the third surfactant is present in an amount from about 3% to about 7% by weight of the formulation. In certain embodiments, the third surfactant is present in an amount of about 3%, about 4%, about 5%, about 6%, or about 7%, by weight of the formulation.

In certain embodiments, the invention relates to any one of the aforementioned formulations, wherein the moisturizer or emollient is selected from the group consisting of panthenol, petrolatum, lactic acid, glycerol, butylene glycol, sodium PCA, sodium hyaluronate, Carbowax 200, Carbowax 400, Carbowax 800, cetyl palmitate, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, dimethicone/divinyldimethicone/silsesquioxance cross polymer, polydimethylsiloxane, caprylic/capric triglyceride, shea butter, jojoba wax, sunflower wax, mimosa wax, phenyl trimethicone, cyclomethicone, $C_{12}$-$C_{15}$ alkyl benzoates, $C_{12}$-$C_{15}$ alkyl ethylhexanoates, dimethiconol, propylene glycol, Theobroma grandiflorum seed butter, ceramide 2, hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, safflower oil, oleyl alcohol, stearic acid, dicaprylate/dicaprate, diethyl sebacate, isostearyl alcohol, pentylene glycol, 1,3-bis(N-2-(hydroxyethyl)palmitoylamino)-2-hydroxypropane, hydrolyzed rice extract, cetyl alcohol, dipalmitoyl hydroxyproline, isononyl isononanoate, and combinations/mixtures thereof.

In certain embodiments, the invention relates to any one of the aforementioned formulations, wherein the moisturizer or emollient is selected from the group consisting of panthenol, glycerol, butylene glycol, sodium hyaluronate, dimethicone/divinyldimethicone/silsesquioxance cross polymer, polydimethylsiloxane, caprylic/capric triglyceride, shea butter, jojoba wax, sunflower wax, mimosa wax, $C_{12}$-$C_{15}$ alkyl ethylhexanoates, allantoin, pentylene glycol, hydrolyzed rice extract, cetyl alcohol, dipalmitoyl hydroxyproline, isononyl isononanoate, and combinations/mixtures thereof.

In certain embodiments, the invention relates to any one of the aforementioned formulations, wherein the moisturizer or emollient is present in an amount from about 12% to about 38% by weight of the formulation. In certain embodiments, the moisturizer or emollient is present in an amount from about 15% to about 35% by weight of the formulation. In certain embodiments, the moisturizer or emollient is present in an amount of about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35% by weight of the formulation.

In certain embodiments, the invention relates to any one of the aforementioned formulations, wherein the moisturizer or emollient comprises isononyl isononanoate in an amount from about 2% to about 9% by weight of the formulation. In certain embodiments, the invention relates to any one of the aforementioned formulations, wherein the moisturizer or emollient comprises isononyl isononanoate in about 2%, about 3%, about 4%, about 5%, about 6%, about 7%, about 8%, or about 9% by weight of the formulation.

In certain embodiments, the invention relates to any one of the aforementioned formulations, wherein the moisturizer or emollient comprises pentylene glycol in an amount from about 0.1% to about 0.4% by weight of the formulation. In certain embodiments, the invention relates to any one of the aforementioned formulations, wherein the moisturizer or emollient comprises pentylene glycol in about 0.1%, about 0.2%, about 0.3%, or about 0.4% by weight of the formulation.

In certain embodiments, the invention relates to any one of the aforementioned formulations, wherein the moisturizer or emollient comprises $C_{12}$-$C_{15}$ alkyl ethylhexanoates in an amount from about 1% to about 6% by weight of the formulation. In certain embodiments, the invention relates to any one of the aforementioned formulations, wherein the moisturizer or emollient comprises $C_{12}$-$C_{15}$ alkyl ethylhexanoates in about 1%, about 1.5%, about 2%, about 2.5%, about 3%, about 3.5%, about 4%, about 4.5%, about 5%, about 5.5%, or about 6% by weight of the formulation.

In certain embodiments, the invention relates to any one of the aforementioned formulations, wherein the moisturizer or emollient comprises jojoba wax, sunflower wax, and mimosa wax, taken together, in an amount from about 1% to about 3% by weight of the formulation. In certain embodiments, the invention relates to any one of the aforementioned formulations, wherein the moisturizer or emollient comprises jojoba wax, sunflower wax, and mimosa wax, taken together, in about 1%, about 1.5%, about 2%, about 2.5%, or about 3% by weight of the formulation.

In certain embodiments, the invention relates to any one of the aforementioned formulations, wherein the moisturizer or emollient comprises shea butter in an amount from about 1% to about 3% by weight of the formulation. In certain embodiments, the invention relates to any one of the aforementioned formulations, wherein the moisturizer or emollient comprises shea butter in about 1%, about 2%, or about 3% by weight of the formulation.

In certain embodiments, the invention relates to any one of the aforementioned formulations, wherein the moisturizer or emollient comprises caprylic/capric triglyceride in an amount from about 1% to about 3% by weight of the formulation. In certain embodiments, the invention relates to any one of the aforementioned formulations, wherein the moisturizer or emollient comprises caprylic/capric triglyceride in about 1%, about 2%, or about 3% by weight of the formulation.

In certain embodiments, the invention relates to any one of the aforementioned formulations, wherein the moisturizer or emollient comprises polydimethylsiloxane in an amount from about 1% to about 3% by weight of the formulation. In certain embodiments, the invention relates to any one of the aforementioned formulations, wherein the moisturizer or emollient comprises polydimethylsiloxane in about 1%, about 2%, or about 3% by weight of the formulation.

In certain embodiments, the invention relates to any one of the aforementioned formulations, wherein the moisturizer or emollient comprises dimethicone/divinyldimethicone/silsesquioxane cross polymer in an amount from about 1% to about 3% by weight of the formulation. In certain embodiments, the invention relates to any one of the aforementioned formulations, wherein the moisturizer or emollient comprises dimethicone/divinyldimethicone/silsesquioxane cross polymer in about 1%, about 2%, or about 3% by weight of the formulation.

In certain embodiments, the invention relates to any one of the aforementioned formulations, wherein the moisturizer or emollient comprises dipalmitoyl hydroxyproline in an amount from about 0.5% to about 1.5% by weight of the formulation. In certain embodiments, the invention relates to any one of the aforementioned formulations, wherein the moisturizer or emollient comprises dipalmitoyl hydroxyproline in about 0.5%, about 0.6%, about 0.7%, about 0.8%, about 0.9%, about 1.0%, about 1.1%, about 1.2%, about 1.3%, about 1.4%, or about 1.5% by weight of the formulation.

In certain embodiments, the invention relates to any one of the aforementioned formulations, wherein the moisturizer or emollient comprises cetyl alcohol in an amount from about 0.5% to about 2.2% by weight of the formulation. In certain embodiments, the invention relates to any one of the aforementioned formulations, wherein the moisturizer or emollient comprises cetyl alcohol in about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, or about 2.2% by weight of the formulation.

In certain embodiments, the invention relates to any one of the aforementioned formulations, wherein the moisturizer or emollient comprises sodium hyaluronates in an amount from about 0.005% to about 0.02% by weight of the formulation. In certain embodiments, the invention relates to any one of the aforementioned formulations, wherein the moisturizer or emollient comprises sodium hyaluronates in about 0.005%, about 0.01%, about 0.015%, or about 0.02% by weight of the formulation.

In certain embodiments, the invention relates to any one of the aforementioned formulations, wherein the moisturizer or emollient comprises panthenol in an amount from about 0.5% to about 1.5% by weight of the formulation. In certain embodiments, the invention relates to any one of the aforementioned formulations, wherein the moisturizer or emollient comprises panthenol in about 0.5%, about 1.0%, or about 1.5% by weight of the formulation.

In certain embodiments, the invention relates to any one of the aforementioned formulations, wherein the moisturizer or emollient comprises butylene glycol and hydrolyzed rice extract, taken together, in an amount from about 0.5% to about 1.5% by weight of the formulation. In certain embodiments, the invention relates to any one of the aforementioned formulations, wherein the moisturizer or emollient comprises butylene glycol and hydrolyzed rice extract, taken together, in about 0.5%, about 1.0%, or about 1.5% by weight of the formulation.

In certain embodiments, the invention relates to any one of the aforementioned formulations, wherein the moisturizer or emollient comprises allantoin in an amount from about 0.2% to about 0.6% by weight of the formulation. In certain embodiments, the invention relates to any one of the aforementioned formulations, wherein the moisturizer or emollient comprises allantoin in about 0.2%, about 0.3%, about 0.4%, about 0.5%, or about 0.6% by weight of the formulation.

In certain embodiments, the invention relates to any one of the aforementioned formulations, wherein the antioxidant or preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid and its esters, sodium bisulfite, butylated hydroxytoluene, butylated hydroxyanisole, tocopherol, tocopheryl acetate, sodium ascorbate/ascorbic acid, ascorbyl palmitate, propyl gallate, disodium EDTA, citric acid, sodium citrate, and (3-(4-chlorophenoxy)-2-hydroxypropyl)carbamate, and combinations/mixtures thereof.

In certain embodiments, the invention relates to any one of the aforementioned formulations, wherein the antioxidant or preservative is selected from the group consisting of potassium sorbate, sodium benzoate, butylated hydroxytoluene, tocopherol, tocopheryl acetate, sodium ascorbate, disodium EDTA, and (3-(4-chlorophenoxy)-2-hydroxypropyl)carbamate, and combinations/mixtures thereof.

In certain embodiments, the invention relates to any one of the aforementioned formulations, wherein the antioxidant or preservative is present in an amount from about 0.8% to about 2.5% by weight of the formulation. In certain embodiments, the antioxidant or preservative is present in an amount of about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4% or about 2.5% by weight of the formulation.

In certain embodiments, the invention relates to any one of the aforementioned formulations, wherein the antioxidant or preservative comprises tocopheryl acetate in an amount from about 0.25% to about 0.75% by weight of the formulation. In certain embodiments, the invention relates to any one of the aforementioned formulations, wherein the antioxidant or preservative comprises tocopheryl acetate in about 0.25%, about 0.30%, about 0.35%, about 0.40%, about 0.45%, about 0.50%, about 0.55%, about 0.60%, about 0.65%, about 0.70%, or about 0.75% by weight of the formulation.

In certain embodiments, the invention relates to any one of the aforementioned formulations, wherein the antioxidant or preservative comprises (3-(4-chlorophenoxy)-2-hydroxypropyl)carbamate in an amount from about 0.15% to about 0.45% by weight of the formulation. In certain embodiments, the invention relates to any one of the aforementioned formulations, wherein the antioxidant or preservative comprises (3-(4-chlorophenoxy)-2-hydroxypropyl)carbamate in about 0.15%, about 0.20%, about 0.25%, about 0.30%, about 0.35%, about 0.40%, or about 0.45% by weight of the formulation.

In certain embodiments, the invention relates to any one of the aforementioned formulations, wherein the antioxidant or preservative comprises sodium ascorbate in an amount from about 0.1% to about 0.4% by weight of the formulation. In certain embodiments, the invention relates to any one of the aforementioned formulations, wherein the antioxidant or preservative comprises sodium ascorbate in about 0.10%, about 0.15%, about 0.20%, about 0.25%, about 0.30%, about 0.35%, or about 0.40% by weight of the formulation.

In certain embodiments, the invention relates to any one of the aforementioned formulations, wherein the antioxidant or preservative comprises tocopherol in an amount from about 0.05% to about 0.25% by weight of the formulation. In certain embodiments, the invention relates to any one of the aforementioned formulations, wherein the antioxidant or preservative comprises tocopherol in about 0.10%, about 0.15%, or about 0.20% by weight of the formulation.

In certain embodiments, the invention relates to any one of the aforementioned formulations, wherein the antioxidant or preservative comprises potassium sorbate in an amount from about 0.05% to about 0.25% by weight of the formulation. In certain embodiments, the invention relates to any one of the aforementioned formulations, wherein the antioxidant or preservative comprises potassium sorbate in about 0.10%, about 0.15%, or about 0.20% by weight of the formulation.

In certain embodiments, the invention relates to any one of the aforementioned formulations, wherein the antioxidant or preservative comprises sodium benzoate in an amount from about 0.05% to about 0.25% by weight of the formulation. In certain embodiments, the invention relates to any one of the aforementioned formulations, wherein the antioxidant or preservative comprises sodium benzoate in about 0.10%, about 0.15%, or about 0.20% by weight of the formulation.

In certain embodiments, the invention relates to any one of the aforementioned formulations, wherein the antioxidant or preservative comprises butylated hydroxytoluene in an amount from about 0.05% to about 0.15% by weight of the formulation. In certain embodiments, the invention relates to any one of the aforementioned formulations, wherein the antioxidant or preservative comprises butylated hydroxytoluene in about 0.05%, about 0.07%, about 0.09%, about 0.11%, about 0.13%, or about 0.15% by weight of the formulation.

In certain embodiments, the invention relates to any one of the aforementioned formulations, wherein the antioxidant or preservative comprises disodium EDTA in an amount from about 0.05% to about 0.15% by weight of the formulation. In certain embodiments, the invention relates to any one of the aforementioned formulations, wherein the antioxidant or preservative comprises disodium EDTA in about 0.05%, about 0.07%, about 0.09%, about 0.11%, about 0.13%, or about 0.15% by weight of the formulation.

In certain embodiments, the invention relates to any one of the aforementioned formulations, wherein the viscosity modifying agent is selected from the group consisting of hydroxyethylcellulose, xanthan gum, sclerotium gum, magnesium aluminum silicate, silica, microcrystalline wax, beeswax, paraffin, and cetyl palmitate and combinations/mixtures thereof.

In certain embodiments, the invention relates to any one of the aforementioned formulations, wherein the viscosity modifying agent is selected from the group consisting of xanthan gum magnesium aluminum silicate and combinations/mixtures thereof.

In certain embodiments, the invention relates to any one of the aforementioned formulations, wherein the viscosity modifying agent is present in an amount from about 0.3% to about 2.6% by weight of the formulation. In certain embodiments, the invention relates to any one of the aforementioned formulations, wherein the viscosity modifying agent is present in about 0.3%, about 0.4%, about 0.5%, about 0.6%, about 0.7%, about 0.8%, about 0.9%, about 1.0%, about 1.2%, about 1.4%, about 1.6%, about 1.8%, about 2.0%, about 2.2%, about 2.4%, or about 2.6% by weight of the formulation.

In certain embodiments, the invention relates to any one of the aforementioned formulations, wherein the viscosity modifying agent comprises magnesium aluminum silicate; and the magnesium aluminum silicate is present in an amount from about 0.3% to about 2.3% by weight of the formulation. In certain embodiments, the magnesium aluminum silicate is present in about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, or about 2.3% by weight of the formulation.

In certain embodiments, the invention relates to any one of the aforementioned formulations, wherein the viscosity modifying agent comprises xanthan gum; and the xanthan gum is present in an amount from about 0.05% to about 0.3% by weight of the formulation. In certain embodiments, the xanthan gum is present in about 0.05%, about 0.1%, about 0.15%, about 0.2%, about 0.25%, or about 0.3% by weight of the formulation.

In certain embodiments, the invention relates to any one of the aforementioned formulations, wherein the pH adjuster is selected from the group consisting of citric acid, sodium hydroxide, and sodium phosphate.

In certain embodiments, the invention relates to any one of the aforementioned formulations, wherein the pH adjuster is sodium hydroxide.

In certain embodiments, the pH adjuster is added to the formulation as a solution. In certain embodiments, the pH adjuster is added to the formulation as a 50% solution.

In certain embodiments, the invention relates to any one of the aforementioned formulations, wherein the pH adjuster is present in an amount from about 0.02% to about 0.06% by weight of the formulation. In certain embodiments, the invention relates to any one of the aforementioned formulations, wherein the pH adjuster is present in an amount from about 0.03% to about 0.05% by weight of the formulation. In certain embodiments, the invention relates to any one of the aforementioned formulations, wherein the pH adjuster is present in about 0.02%, about 0.03%, about 0.04%, about 0.05%, or about 0.06% by weight of the formulation.

In certain embodiments, the invention relates to any one of the aforementioned formulations, wherein the sodium hydroxide is present in an amount from about 0.02% to about 0.06% by weight of the formulation. In certain embodiments, the invention relates to any one of the aforementioned formulations, wherein the sodium hydroxide is present in an amount from about 0.03% to about 0.05% by weight of the formulation. In certain embodiments, the invention relates to any one of the aforementioned formulations, wherein the sodium hydroxide is present in about 0.02%, about 0.03%, about 0.04%, about 0.05%, or about 0.06% by weight of the formulation.

In certain embodiments, the invention relates to any one of the aforementioned formulations, wherein the formulation further comprises an additional constituent. In certain embodiments, the additional constituent is selected from the group consisting of skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents, binders/excipients, buffering agents, chelating agents, film forming agents, conditioning agents, opacifying agents, lipids, anti-inflammatory agents, and immunomodulators, and combinations thereof.

In certain embodiments, the additional constituent is selected from the group consisting of palmitoyl dipeptide-5 diaminobutyloyl hydroxythreonine and palmitoyl dipeptide-6 diaminohydroxybutyrate, and combinations thereof. In certain embodiments, the palmitoyl dipeptide-5 diaminobutyloyl hydroxythreonine and palmitoyl dipeptide-6 diaminohydroxybutyrate are combined with glycerin. In certain embodiments, the palmitoyl dipeptide-5 diaminobutyloyl hydroxythreonine, palmitoyl dipeptide-6 diaminohydroxybutyrate, and glycerin, taken together, are present in from about 0.5% to about 1.5% by weight of the formulation. In certain embodiments, the palmitoyl dipeptide-5 diaminobutyloyl hydroxythreonine, palmitoyl dipeptide-6 diaminohydroxybutyrate, and glycerin, taken together, are present in about 0.5%, about 0.6%, about 0.7%, about 0.8%, about 0.9%, about 1.0%, about 1.1%, about 1.2%, about 1.3%, about 1.4%, or about 1.5% by weight of the formulation.

In certain embodiments, the additional constituent is algae extract and mugwort extract. In certain embodiments, the algae extract and mugwort extract, taken together, are present in from about 0.5% to about 1.5% by weight of the formulation. In certain embodiments, algae extract and mugwort extract, taken together, are present in about 0.5%, about 0.6%, about 0.7%, about 0.8%, about 0.9%, about 1.0% about In certain embodiments, the additional constituent is stearyl glycyrrhetinate. In certain embodiments, the stearyl glycyrrhetinate is present in an amount from about 0.05% to about 0.15% by weight of the formulation. In certain embodiments, the stearyl glycyrrhetinate is present in about 0.05%, about 0.06%, about 0.07%, about 0.08%, about 0.09%, about 0.10%, about 0.11%, about 0.12%, about 0.13%, about 0.14%, or about 0.15% by weight of the formulation.

In certain embodiments, the additional constituent is bisabolol. In certain embodiments, the bisabolol is present in an amount from about 0.1% to about 0.3% by weight of the formulation. In certain embodiments, the bisabolol is present in about 0.1%, about 0.15%, about 0.2%, about 0.25%, or about 0.3% by weight of the formulation.

In certain embodiments, the additional constituent is bergamot. In certain embodiments, the bergamot is present in an amount from about 0.15% to about 0.45% by weight of the formulation. In certain embodiments, the bergamot is present in about 0.15%, about 0.2%, about 0.25%, about 0.3%, about 0.35%, about 0.4%, or about 0.45% by weight of the formulation.

In certain embodiments, the additional constituent is tetrahexyldecyl ascorbate. In certain embodiments, the tetrahexyldecyl ascorbate is present in an amount from about 0.25% to about 0.75% by weight of the formulation. In certain embodiments, the tetrahexyldecyl ascorbate is present in about 0.25%, about 0.3%, about 0.35%, about 0.4%, about 0.45%, about 0.5%, about 0.55%, about 0.6%, about 0.65%, about 0.7%, or about 0.75% by weight of the formulation.

In certain embodiments, the additional constituent is palmitoyl-lysyl-valyl-lysine bistrifluoroacetate. In certain embodiments, the palmitoyl-lysyl-valyl-lysine bistrifluoroacetate is combined with glycerin. In certain embodiments, the palmitoyl-lysyl-valyl-lysine bistrifluoroacetate and glycerin, taken together, are present in an amount from about 1% to about 4% by weight of the formulation. In certain embodiments, the palmitoyl-lysyl-valyl-lysine bistrifluoroacetate and glycerin, taken together, are present in about 1%, about 1.5%, about 2%, about 2.5%, about 3%, about 3.5%, or about 4% by weight of the formulation.

In certain embodiments, the additional constituent is niacinamide. In certain embodiments, the niacinamide is present in an amount from about 0.5% to about 1.5% by weight of the formulation. In certain embodiments, the niacinamide is present in about 0.5%, about 0.6%, about 0.7%, about 0.8%, about 0.9%, about 1.0%, about 1.1%, about 1.2%, about 1.3%, about 1.4%, or about 1.5% by weight of the formulation.

Exemplary Foam-Forming Compositions of the Invention

In certain embodiments, the invention relates to a foam-forming composition, comprising: any one of the aforementioned formulations; and a propellant.

In certain embodiments, the invention relates to a foam-forming composition, consisting essentially of: any one of the aforementioned formulations; and a propellant.

In certain embodiments, the invention relates to a foam-forming composition, consisting of: any one of the aforementioned formulations; and a propellant.

In certain embodiments, the invention relates to a foam-forming composition, comprising: any one of the aforementioned formulations; a propellant; and a purge gas.

In certain embodiments, the invention relates to a foam-forming composition, consisting essentially of: any one of the aforementioned formulations; a propellant; and a purge gas.

In certain embodiments, the invention relates to a foam-forming composition, consisting of: any one of the aforementioned formulations; a propellant; and a purge gas.

Exemplary Propellants

As outlined above, in certain embodiments, the invention relates to a foam-forming composition comprising a formulation, a propellant, and a purge gas. The propellants described below may be present in any one of the aforementioned foam-forming compositions.

In certain embodiments, the invention relates to any one of the aforementioned foam-forming compositions, wherein the propellant is selected from the group consisting of 1,1,1,2-tetrafluoroethane, 1,1,1,2,3,3,3-heptafluoropropane, 1,3,3,3-tetrafluoropropene, and combinations/mixtures thereof.

In certain embodiments, the invention relates to any one of the aforementioned foam-forming compositions, wherein the propellant is present in an amount from about 2% to about 50% by weight of the foam-forming composition. In certain embodiments, the invention relates to any one of the aforementioned foam-forming compositions, wherein the propellant is present in an amount from about 5% to about 30% by weight of the foam-forming composition. In certain embodiments, the invention relates to any one of the aforementioned foam-forming compositions, wherein the propellant is about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight of the foam-forming composition.

Exemplary Purge Gases

As outlined above, in certain embodiments, the invention relates to a foam-forming composition comprising a formulation, a propellant, and a purge gas. The purge gases described below may be present in any one of the aforementioned foam-forming compositions.

In certain embodiments, the invention relates to any one of the aforementioned compositions, wherein the purge gas is selected from the group consisting of nitrogen and argon. In certain embodiments, the invention relates to any one of the aforementioned compositions, wherein the purge gas is argon.

In certain embodiments, the invention relates to any one of the aforementioned compositions, wherein the purge gas is present in an amount from about 0.4% to about 6% by weight of the composition. In certain embodiments, the invention relates to any one of the aforementioned compositions, wherein the purge gas is present in an amount from about 0.8% to about 5% by weight of the composition. In certain embodiments, the invention relates to any one of the aforementioned compositions, wherein the purge gas is about 0.8%, about 1%, about 1.2%, about 1.4%, about 1.6%, about 1.8%, about 2%, about 2.2%, about 2.5%, about 2.6%, about 2.8%, about 3%, about 3.2%, about 3.4%, about 3.6%, about 3.8%, about 4%, about 4.2%, about 4.4%, about 4.6%, about 4.8% or about 5% by weight of the composition.

Exemplary Properties of Formulations of the Invention

In certain embodiments, the invention relates to any one of the aforementioned formulations, wherein the formulation is semi-solid.

In certain embodiments, the invention relates to any one of the aforementioned formulations, wherein the formulation is a cream.

In certain embodiments, the invention relates to any one of the aforementioned formulations, wherein the formulation is a gel.

In certain embodiments, the invention relates to any one of the aforementioned formulations that, upon expulsion from an aerosol container, forms a foam. In certain embodiments, the foam is temperature-stable. In certain embodiments, the foam is time-stable. In certain embodiments, the density of the foam is from about 0.05 to about 0.5 g/cm$^3$. In certain embodiments, the invention relates to any one of the aforementioned formulations that is easily shaken in an aerosol container. In certain embodiments, the invention relates to any one of the aforementioned formulations that is easily dispensed from an aerosol container.

In certain embodiments, the invention relates to any one of the aforementioned formulations that, upon application to the skin of an affected subject, is non-irritating.

In certain embodiments, the invention relates to any one of the aforementioned formulations that, upon application to the skin of an affected subject, is well-tolerated.

In certain embodiments, the invention relates to any one of the aforementioned formulations that, upon application to the skin of an affected subject, reduces inflammation.

In certain embodiments, the invention relates to any one of the aforementioned formulations that, upon application to the skin of an affected subject, is non-cytotoxic.

In certain embodiments, the invention relates to any one of the aforementioned formulations that, upon application to the skin of an affected subject, is weakly sensitizing. In certain embodiments, the invention relates to any one of the aforementioned formulations that, upon application to the skin of an affected subject, is non-sensitizing.

In certain embodiments, the invention relates to any one of the aforementioned formulations that, upon application to the skin of an affected subject, does not produce edema or erythema.

In certain embodiments, the invention relates to any one of the aforementioned formulations that, upon application to the skin of an affected subject, moisturizes the skin.

In certain embodiments, the invention relates to any one of the aforementioned formulations that, upon application to the skin of an affected subject, increases hydration of the skin.

In certain embodiments, the invention relates to any one of the aforementioned formulations that, upon application to the skin of an affected subject, reduces transepidermal water loss.

Exemplary Formulations of the Invention for Particular Uses

In certain embodiments, the invention relates to any one of the formulations for use in the treatment or prevention of a skin disorder.

In certain embodiments, the invention relates to any one of the aforementioned formulations for use in the treatment or prevention of a skin disorder, wherein the emulsion or composition is formulated for topical application once daily or twice daily.

In certain embodiments, the skin disorder is acne vulgaris or keratosis pilaris.

In certain embodiments, the skin disorder is skin aging. In certain embodiments, the treatment or prevention of skin aging includes the treatment or prevention of wrinkles, sun spots, dullness, fine lines, increased pore size, or uneven skin tone.

Exemplary Methods of Use

In certain embodiments, the invention relates to a method of treating a skin disorder, comprising the step of applying to an affected area of a subject in need thereof a therapeutically-effective amount of any one of the aforementioned formulations.

In one embodiment, the present invention relates to any one of the above-mentioned methods, wherein the subject is human.

In one embodiment, the present invention relates to any one of the above-mentioned methods, wherein the composition is applied once daily.

In one embodiment, the present invention relates to any one of the above-mentioned methods, wherein the composition is applied twice daily.

In certain embodiments, the present invention relates to any one of the above-mentioned methods, wherein the skin disorder is acne vulgaris or keratosis pilaris.

In certain embodiments, the present invention relates to any one of the above-mentioned methods, wherein the skin disorder is skin aging. In certain embodiments, the present invention relates to any one of the above-mentioned methods, wherein the treatment or prevention of skin aging includes the treatment or prevention of wrinkles, sun spots, dullness, fine lines, increased pore size, or uneven skin tone.

Exemplary Methods of Making Formulations of the Invention

In certain embodiments, the invention relates to a method of making any one of the aforementioned formulations, comprising the step of combining any one of the aforementioned active agent-containing microemulsions with the a moisturizer or emollient, the third surfactant, the antioxidant or preservative, the viscosity modifying agent; and the pH adjuster.

In certain embodiments, the invention relates to a method of making any one of the aforementioned formulations, comprising the steps described in Example 4.

EXEMPLIFICATION

The invention now being generally described, it will be more readily understood by reference to the following examples which are included merely for purposes of illustration of certain aspects and embodiments of the present invention, and are not intended to limit the invention.

Example 1

Spontaneous Microemulsion Formation by Mixtures of a Caprylocaproyl Polyethylene Glycol-Based Surfactant and Cyclodextrin in Aqueous Media Microemulsion Preparation:
Any two components (examples: Labrasol®-water, HPXCD-water, or Labrasol®-HPXCD) were mixed (in different ratios) in different scintillation vials and then the third component was titrated to each vial until a clear-to-turbid or turbid-to-clear transition occurred (in simple situations). Finally wt % percentages data for each component (Labrasol®, water, and cyclodextrin) were plotted to construct the ternary phase diagram. See FIG. 2.

In FIG. 3, the "water" phase (above) was replaced with an "aqueous" phase. An example of an aqueous phase is shown in FIG. 5.

Example 2

Solubility/Dispersibility of Retinol in the Labrasol®-HPGCD-Water Systems and in Labrasol®, HPGCD, and Water, Individually Materials
Drug used: 1. Solid Retinol (98%) from Sigma, 2. Retistar (5% Retinol, caprylic/capric triglyceride, sodium ascorbate, Tocopherol) from BASF, 3. Retinol 50C (50% retinol, ethoxylated sorbitan monolaurate (Tween 20), butylated hydroxytoluene (BHT), 2-(1,1-dimethylethyl)-4-methoxy-phenol) from BASF.
Cyclodextrin used: hydroxypropyl-X-cyclodextrin (X=alpha, beta, or gamma).
Methods
Vial L from FIG. 4(a) shows the formation of a novel microemulsion (clear transparent system) as well as complete miscibility of Retistar (final retinol concentration: 0.06%) in Labrasol®-HPGCD-water microemulsion system (Note: capric/caprylic triglycerides coming from the Retistar are also contributing to the microemulsion system). The miscibility of retinol may be attributed to the drug incorporation in the cyclodextrin system as well as the micro emulsion system.

Vial labeled 8 from FIG. 4(b) shows the formation of a novel microemulsion (clear transparent system) as well as complete miscibility of Retinol 50C (final retinol concentration: 1.2%) in Labrasol®-HPGCD-water microemulsion system (Note: ethoxylated sorbitan monolaurate coming from the Retinol 50C are also contributing to the microemulsion system). The miscibility of Retinol may be attributed to the drug incorporation in the cyclodextrin system as well as in the microemulsion system.

Vial labeled 1 from FIG. 4(c) shows the formation of a novel microemulsion (clear transparent system) as well as complete miscibility of solid retinol (final retinol concentration: 1.2%) in Labrasol®-HPGCD-water microemulsion system. This miscibility of retinol may be attributed to the drug incorporation in the cyclodextrin system as well as in the microemulsion system Retinol is incorporated in the cyclodextrin system as well as in the microemulsion system.

Example 3

Encapsulation of Pharmaceutical/Cosmetic Ingredients in CD-Stabilized Microemulsions Materials
Retinol used: 1. Solid retinol (98%) from Sigma, 2. Retistar (5% retinol, caprylic/capric triglyceride, sodium ascorbate, tocopherol) from BASF, 3. Retinol 50C (50% retinol, ethoxylated sorbitan monolaurate, BHT, 2-(1,1-dimethylethyl)-4-methoxy-phenol from BASF
Methods
Microemulsion Preparation:
Any two components (examples: Labrasol®-water, cyclodextrin-water, or Labrasol®-HPBCD) were mixed (in different ratios) in different scintillation vials and then the third component was titrated to each vial until a clear-to-turbid or turbid-to-clear transition occurred (in simple situations). Finally wt % percentages data for each component (Labrosol, water, and cyclodextrin) were plotted to construct the ternary phase diagram.
Incorporation of Drug:
Drug can be dissolved in the individual components or any of the two-component combination systems, followed by microemulsion formulation. Alternatively Drug can be directly added to the previously prepared microemulsion phase followed by shaking until a clear solution is achieved (when the achievable drug concentration is known previously).
See FIG. 7.

Example 4

Retinol Cream

A 0.5% retinol cream base was formulated, which was then used for making an aerosol foam product. The composition is shown in FIG. 10, and the method of formulation is outlined below.

Stepwise strategies for making a semi-solid formulation using a cyclodextrin-based microemulsion that was used to make the 0.5% retinol product.

Figure 8:
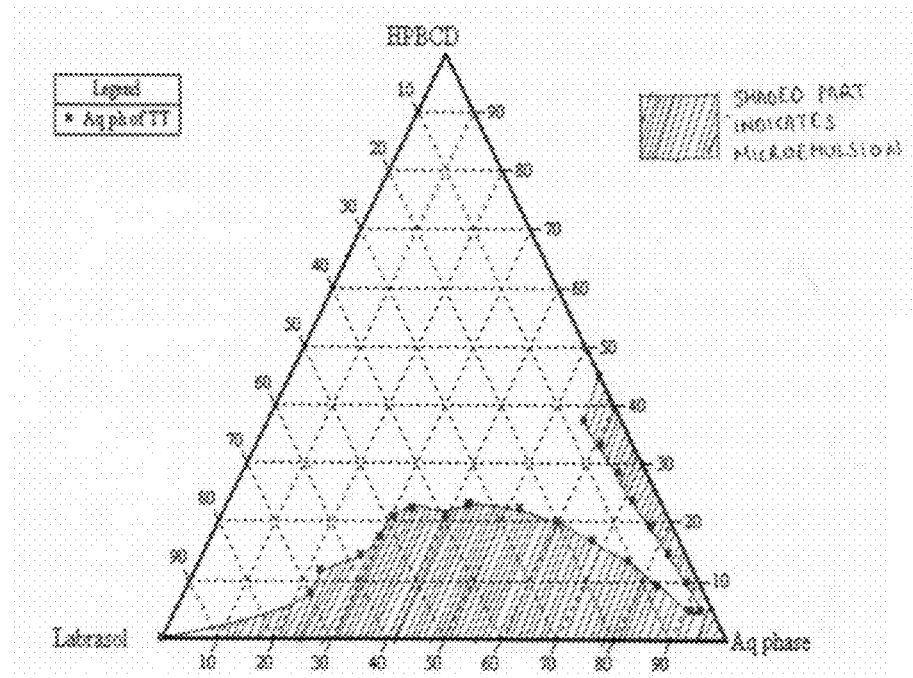
FIG. 8 depicts a ternary phase diagram developed from systems with Labrasol®, HPBCD, and aqueous phase (see FIG. 10 for composition). The shaded portions indicate the existence of micro emulsions.
Figure 9:
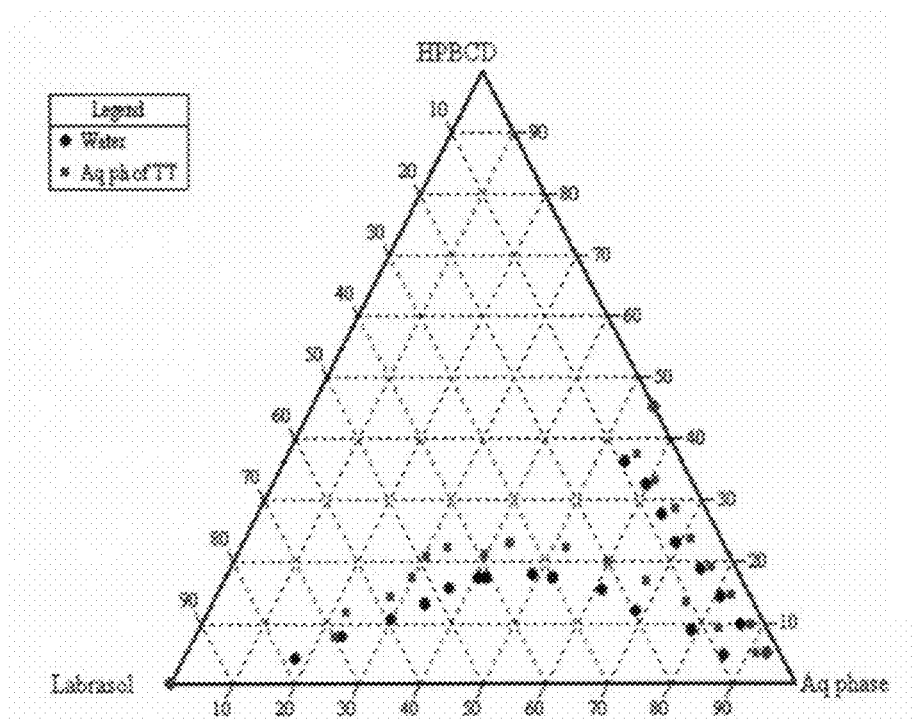
FIG. 9 depicts a ternary phase diagram developed from systems with Labrasol®, HPBCD, and (1) aqueous phase (squares; see FIG. 10 for composition) or (2) pure water (black circles).

Step 1. Construction of the microemulsion phase diagram replacing water with an aqueous phase of the formulation (FIG. 8).

Step 2. Preparation of a microemulsion based on a composition selected from the clear zone of the phase diagram of Labrasol®-HPXCD-aqueous solution system.

Figure 11:
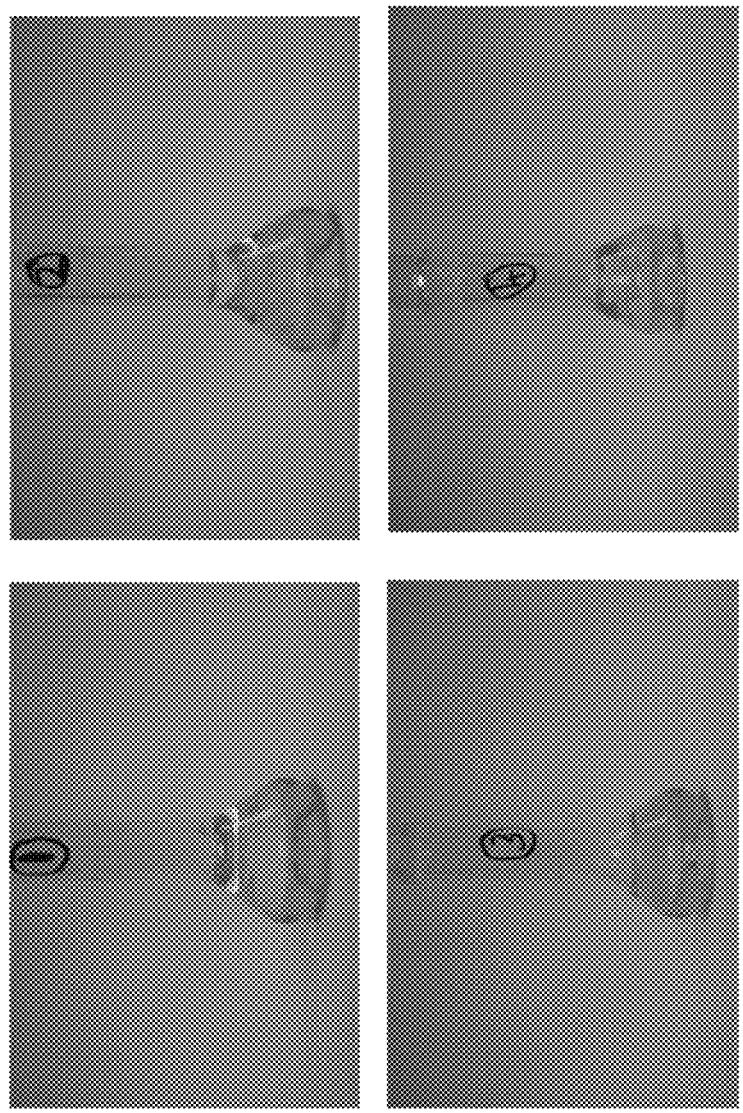
FIG. 11 depicts the compatibility of the microemulsion (bottom phase of each picture; 1.2% retinol in Labrasol®-HPGCD-aqueous solution, 80:5:15) with the oil that may be present in the oil phase of a cream formulation (top phase of each picture; 1=light mineral oil; 2=isononyl isononanoate; 3=silicon oil; and 4=isopropyl myristate).

Step 3. Immiscibility/compatibility test: Compatibility between the prepared microemulsion and the liquid oily phase of the targeted cream formulation was tested (FIG. 11). It was observed that the microemulsion remained intact in the presence of oil coming from the oil phase of the cream. This test was repeated using other oils. A desirable oil is one that does not destabilize the microemulsion.

Figure 12:
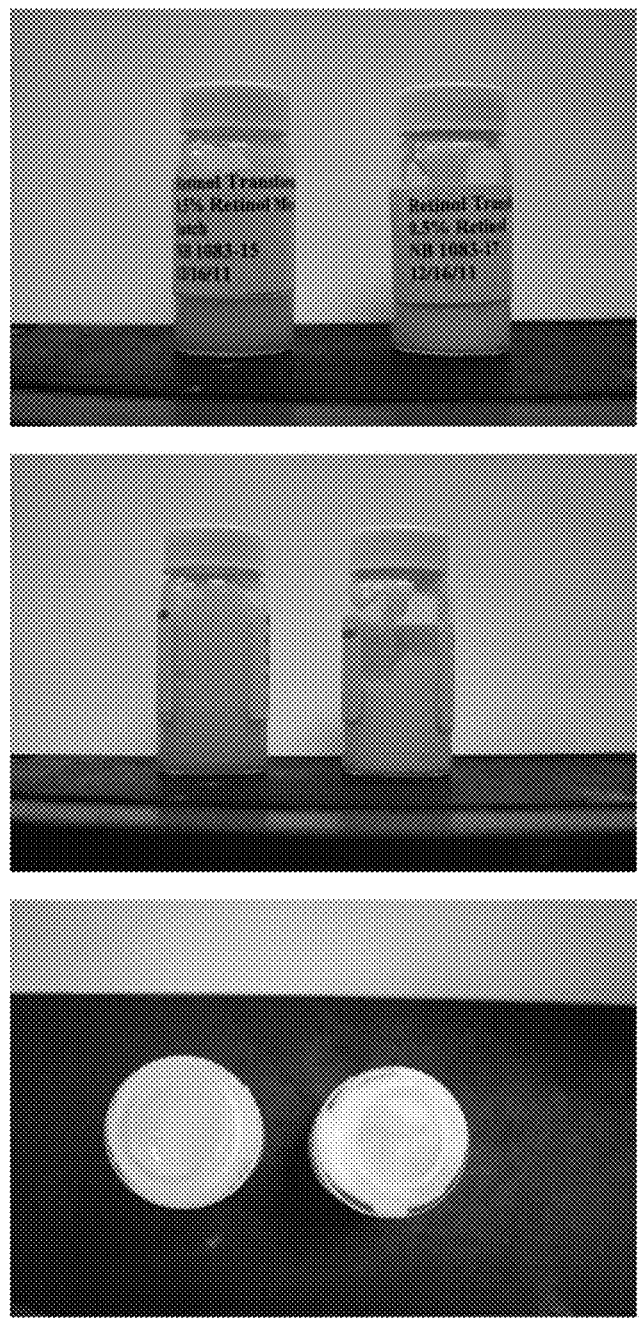
FIG. 12 depicts (left) a finished cream product containing 0.5% retinol encapsulated in a HPGCD-based microemulsion base; and (right) a corresponding control (0.5% retinol product without microemulsion).

Step 4. Appropriate procedure was designed to formulate the final cream formulation (refer to FIG. 10). FIG. 12 shows the visual appearance of the cyclodextrin-based cream and the corresponding control (without microemulsion).

Procedure for making the final cream formulation (see FIG. 10):

Phase A:
1. Weigh all ingredients from Phase A into a glass beaker.
2. Heat and mix to 60° C. and hold at 60° C. with continuous mixing with a spatula. Use a water bath to get uniform heating.

Phase B:
1. In a beaker add microemulsion system at room temperature
2. Place beaker under the homogenizer and while mixing rapidly sprinkle in Veegum K granules being careful to avoid lumps
3. Homogenize phase B for 5 minutes.

Phase C:
1. At room temperature, weigh phase C ingredients into a beaker
2. Mix until all the xanthan gum is fully wetted out and lump free Phase D:
1. Weigh out the ingredients of Phase D into a small beaker and transfer to Phase BC (see Procedure below) at room temperature Phase E:
1. At 45° C. individually add phase E to the batch and mix until uniform Phase F:
1. In a small beaker combine phase F
2. Heat and mix phase F to 50° C.
3. Mix until all of the chlorphenesin is dissolved Phase G:
1. Weigh ingredients into a beaker and thoroughly mix together Phase H:
1. Already added as Phase B.

Phase I:
1. Take out the fragrance from refrigerator and let it come to room temperature Procedure:
1. After Homogenizing Phase B, mix it with Phase C for 15 minutes until fully hydrated on the lightning mixer. Keep an argon blanket on during the entire batch making process.
2. Add Phase D to the above mixture and then heat and mix phase BCD to 50° C.
3. Making sure that phase A is at 60° C. and continuously mixing, transfer phase A into phase BCD at 50° C.
4. Once fully transferred homogenize the batch for 3 minutes
5. Then turn off the homogenizer and by using only the lightning mixer cool the batch to 45° C. (no water bath).
6. At 45° C. individually add phase E to the batch and mix until uniform
7. Then add phase F to the batch at 45° C. and mix and cool batch to 32-30° C. (no water bath)
8. Add Phase G to the formulation at 30° C.
9. Slowly add fragrance while batch is mixing on lightning mixer and keep batch covered
10. QS batch once it is at 25° C.
11. Versate (whip-mix) the entire batch and place in a suitable container protected from light. Blanket headspace the container with argon and seal.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A microemulsion, consisting essentially of: an aqueous phase; a first surfactant; and a second surfactant, wherein the first surfactant is a cyclodextrin, the second surfactant comprises caprylocaproyl macrogol-8 glycerides or caprylocaproyl polyoxyl-8 glycerides, and the aqueous phase comprises a moisturizer or emollient and an anti-inflammatory agent.
2. The microemulsion of claim 1, wherein the aqueous phase is present in an amount from about 75% to about 95% by weight of the microemulsion.
3. The microemulsion of claim 1, wherein the moisturizer or emollient is selected from the group consisting of panthenol, allantoin, sodium hyaluraonate, pentylene glycol, and combinations/mixtures thereof.
4. The microemulsion of claim 1, wherein the moisturizer or emollient is present in an amount from about 0.8% to about 2.3% by weight of the aqueous phase.
5. The microemulsion of claim 1, wherein the anti-inflammatory agent is niacinamide.
6. The microemulsion of claim 1, wherein the anti-inflammatory agent is present in an amount from about 0.5% to about 2% by weight of the aqueous phase.
7. The microemulsion of claim 1, wherein the aqueous phase comprises an antioxidant or preservative.
8. The microemulsion of claim 1, wherein the antioxidant or preservative is selected from the group consisting of potassium sorbate, sodium benzoate, disodium EDTA, and combinations/mixtures thereof.
9. The microemulsion of claim 1, wherein the antioxidant or preservative is present in an amount from about 0.2% to about 0.6% by weight of the aqueous phase.
10. The microemulsion of claim 1, wherein the aqueous phase comprises a pH adjuster.
11. The microemulsion of claim 10, wherein the pH adjuster is sodium hydroxide.
12. The microemulsion of claim 10, wherein the pH adjuster is present in an amount from about 0.02% to about 0.1% by weight of the aqueous phase.
13. The microemulsion of claim 1, wherein the first surfactant is present in an amount from about 1% to about 8% by weight of the microemulsion.
14. The microemulsion of claim 1, wherein the first surfactant is hydroxypropyl α-cyclodextrin, hydroxypropyl β-cyclodextrin, or hydroxypropyl γ-cyclodextrin.
15. The microemulsion of claim 1, wherein the first surfactant is hydroxypropyl β-cyclodextrin.
16. The microemulsion of claim 1, wherein the second surfactant is present in an amount from about 4% to about 22% by weight of the microemulsion.
17. The microemulsion of claim 1 wherein the cyclodextrin is hydroxypropyl β-cyclodextrin, the cyclodextrin is present in an amount of about 5% by weight of the microemulsion; and
the caprylocaproyl macrogol-8 glycerides or caprylocaproyl polyoxyl-8 glycerides, is present in an amount of about 15% by weight of the microemulsion.

18. The microemulsion of claim 1 wherein the cyclodextrin is hydroxypropyl β-cyclodextrin, the cyclodextrin is present in an amount of about 3% by weight of the microemulsion; and the caprylocaproyl macrogol-8 glycerides or caprylocaproyl polyoxyl-8 glycerides, is present in an amount of about 7% by weight of the microemulsion.

19. A method of making a microemulsion of claim 1, comprising the step of combining the aqueous phase, the first surfactant, and the second surfactant.

* * * * *